(12) United States Patent
Rohrer et al.

(10) Patent No.: US 6,335,174 B1
(45) Date of Patent: Jan. 1, 2002

(54) ONCOFETAL ANTIGEN SPECIFIC T-LYMPHOCYTE MEDIATED IMMUNE RESPONSE: MANIPULATION AND USES OF ONCOFETAL ANTIGEN SPECIFIC CD4, CD8 CYTOTOXIC AND SUPPRESSOR T CELLS AND INTERLEUKIN-10

(75) Inventors: James W. Rohrer; Joseph H. Coggin, Jr.; Adel L. Barsoum, all of Mobile, AL (US)

(73) Assignee: South Alabama Medical Science Foundation, Mobile, AL (US)

( * ) Notice: Subject to any disclaimer, the term of this patent is extended or adjusted under 35 U.S.C. 154(b) by 0 days.

(21) Appl. No.: 08/835,069

(22) Filed: Apr. 4, 1997

Related U.S. Application Data

(60) Provisional application No. 60/014,903, filed on Apr. 5, 1996.

(51) Int. Cl.$^7$ .............................................. G01N 35/574
(52) U.S. Cl. .................. 435/7.23; 435/7.24; 435/29; 435/372.3; 435/975; 530/351; 530/388.75
(58) Field of Search ............... 435/2, 29, 975, 435/4, 7.23, 7.24, 325, 355, 372.3, 405; 530/350, 828, 351, 388.75; 424/277.1, 93.71, 534

(56) References Cited

U.S. PATENT DOCUMENTS 4,610,878 A 9/1986 Wilson et al.
4,686,180 A 8/1987 Coggin, Jr. et al.

(List continued on next page.)

OTHER PUBLICATIONS

Abou–Zeid, et al., J. Immunol. Methods 98:5 (1987).
Bain and Pshyk, Transplantation Proc. 4:163 (1972).
Barsoum et al., J. Biol. Resp. Modifiers 8:579 (1989).
Barsoum et al., Inter. J. Cancer 48:248–252.
Barsoum et al., Int. J. Biochem. 24:483–489 (1993).
Berg, et al., J. Immunol. 146:2865 (1991).
Bost, et al., J. Immunol. 154:718 (1995).
Boyum, Nature 204:793 (1964).
Chang, et al., Critical Reviews in Oncology/Hematology 22:213–228 (1996).
Chen, et al., Cell 71:1093 (1992).
Coggin, et al., Am J. Pathol 130:136 (1988).
Coggin, et al., Internat. J. Rad. Biol. 71:81 (1997).
Coggin, et al., Anti–Cancer Res. 19:5535 (1999).

(List continued on next page.)

Primary Examiner—Patrick J. Nolan
(74) Attorney, Agent, or Firm—Lerner, David, Littenberg, Krumholz & Mentlik, LLP

(57) ABSTRACT

The present invention provides a method of determining the success of a cancer therapy in an individual, comprising the step of measuring the frequency of occurence of an oncofetal antigen-specific subclasses in the individual's peripheral blood. Also provided is a method of determining whether protective immunity against a tumor will develop in an individual, comprising the step of measuring the frequency of oncofetal antigen-specific T cells, tumor cells and macrophages at the site of the tumor which secrete IL-10. Additionally, a method of determining whether an individual having a tumor will go into remission or remain in remission, comprising the step of measuring the frequency of oncofetal antigen-specific Th1 cells, Tc cells and Ts cells, IL-10 and interferon-γ secreting T cells in the peripheral blood.

2 Claims, 8 Drawing Sheets

U.S. PATENT DOCUMENTS

| | | | |
|---|---|---|---|
| 4,746,539 A | 5/1988 | Webb et al. | 424/85 |
| 5,180,809 A | 1/1993 | Ruoslahti et al. | 530/350 |
| 5,525,461 A | 6/1996 | Rittershaus | |
| 5,656,444 A | 8/1997 | Webb et al. | 435/7.23 |
| 5,688,505 A | 11/1997 | Webb et al. | 424/145.1 |

OTHER PUBLICATIONS

Coggin, Shared Cross–Protective OFAs on Chemically Induced Rodent Sarcomas. Immunology Today 10(3):76–78 (1989).
Coggin, Molecular Biotheraphy 1(4):223–228 (1989).
Coggin, et al., Archives of Otolaryngology–Head and Neck Surgery 119:1257–1266 (1993).
Cone, et al., J. Clin. Invest. 43:2241 (1964).
Cox, Intern. J. Rad. Biol. 65:57–64 (1994).
Damle, et al., Immunol. 148:1985 (1992).
Decker, et al., J. Immunol. Methods 15:61 (1988).
DeSantis, et al., Eur. J. Immunol. 15:575 (1987).
De Waal, et al., J. Exp. Med. 174:1209 (1991).
De Waal, et al., J. Immunol. 150:4754 (1993).
Fairchild, et al., J. Immunol. 145:2001 (1990).
Ferguson, et al., J. Exp. Med. 179:1597 (1994).
Fiorentino, et al., J. Exp. Med. 170:2081 (1989).
Fiorentino, et al., J. Immunol. 146:3444 (1991).
Fotino, et al., Ann. Clin. Lab. Sci. 1:131 (1971).
Fotino, et al., Vox Sang 21:469 (1971).
Gajewski, et al., J. Immunol. 140:4245 (1988).
Gershon, et al., Nature 213:674 (1967).
Harding, et al., Nature 356:607 (1992).
Harris, et al., Brit. J. Haematol. 18:229 (1970).
Hellstrom, et al., Int. J. Cancer 21:317 (1978).
Henderson, et al., Advances in Immunology 62:217–256 (1996).
Johnson, et al., J. Immunol. 152:429 (1994).
Jung, et al., J. Immunol. Methods 159:197 (1993).
Kavanaugh, et al., Hematology/Oncology Clinics of North America, 4:927–951 (1996).
Leffel, et al., Cancer Res. 37:4112 (1977).
Levy, et al., Critical Reviews in Immunology 16:31–57 (1996).
Li, et al., J. Immunol. 153:3967 (1994).
Lombardi, et al., Science 264:1587 (1994).
Lynch, et al., Eur. J. Immunol. 21:1403 (1991).
Moller, Scand. J. Immunol. 27:247 (1988).
North, et al., J. Exp. Med. 145:275 (1977).
O'Garra, et al., Eur. J. Immunol. 22:711 (1992).
Payne, et al., J. Natl. Cancer Inst. 75:527 (1985).
Phillips, In: Tissue Culture:Methods and Applications. P. F. Kruse, Jr., ed. Academic Press, New York, 406–408 (1994).
Portsmann, et al., J. Immunol. Methods 82:169 (1985).
Powrie, et al., Eur. J. Immunol. 23:2223 (1993).
Rabin, et al., J. Immunol. 127:1852 (1981).
Rashid, et al., J. Natl. Cancer Inst. 86:515–526 (1994).
Renie, et al., Sci. Amer. Sep. 57–59 (1996).
Restifo, et al., J. Immunol. 147:1453 (1993).
Rivas, et al., J. Immunol. 149:3865 (1992).
Rogers, et al., J. Immunol. Methods 15:61 (1991).
Rohrer, et al., J. Natl. Cancer Inst. 84:602 (1992).
Rohrer, et al., J. Immunol. 152:754–764 (1994).
Rohrer, et al., J. Immunol. 154:2266 (1995).
Rohrer, et al., J. Immunol. 155:5719 (1995).
Schadene, et al., J. Immunol. 152:4368 (1994).
Schwartz, Science 248:1349 (1990).
Smith, et al., Am. J. Pathol. 145:18 (1994).
Stranding, et al., Biochem. Biophys. Acta 508:85 (1978).
Stephenson, et al., Surgery 105:523.
Ting, et al., Vox Sang. 20:561 (1971).
Vaage, Cancer Res. 31:1655 (1971).
Vikingson, et al., J. Immunol. Methods 173:219 (1994).
Vose, et al., Int. J. Cancer 245:579 (1979).
Wepsic, et al., J. Natl. Cancer Inst. 44:955 (1970).
Wybran, et al., J. Immunol. 110:1157 (1973).
Wysocki, et al., Proc. Natl. Acad. Sci. USA 75:2844 (1978).
Yu et al., N. Engl. J. Med. 297:121 (1977).
Zheng, et al., Proc. Natl. acad. Sci USA 86:3758 (1989).
Zarling, et al., Cancer Immun. Immunother. 7:243 (1980).
Naor et al., Annals New York Acad. Sci. 636:135–146 (1991).
Mazzocchi et al., Int. J. Cancer 58:330–339 (1994).
Berman, et al., J. Immunol. 157(1) :231–238 (1996).
Rohrer, J. W. et al. J. Immunol. 154 (5): 2266–2280, Mar. 1995.*
Wang, L. et al. Cell. Immunol. 159: 152–169, Dec. 1994.*
Kim, J. et al. J. Immunol. 155 (4): 2240–2247, Aug. 1995.*
Yssel, H. et al. J. Immunol. 149 (7): 2378–2384, Oct. 1992.*
Inoue, T. et al. J. Immunol. 150 (6): 2121–2138, Mar. 1993.*
Totterman, T. et al. Blood 74 (2): 786–792, Aug. 1992.*
Giovarelli, M. et al. J. Immunol. 155 (6): 3112–3123, Sep. 1995.*
Yang, G. et al. J. Immunol. 155 (8): 3897–3903, Oct. 1995.*
Berman, R. et al. J. Immunol. 155 (8): 3897–3903, Oct. 1993.*

* cited by examiner

ONCOFETAL ANTIGEN SPECIFIC T-LYMPHOCYTE MEDIATED IMMUNE RESPONSE: MANIPULATION AND USES OF ONCOFETAL ANTIGEN SPECIFIC CD4, CD8 CYTOTOXIC AND SUPPRESSOR T CELLS AND INTERLEUKIN-10

This application claims priority to provisional application U.S. Ser. No. 60/014,903, filed Apr. 5, 1996.

FEDERAL FUNDING LEGEND

This invention was produced in part using funds obtained through a grant from the National Institutes of Health. Consequently, the federal government has certain rights in this invention.

BACKGROUND OF THE INVENTION

1. Field of the Invention

The present invention relates generally to the fields of immunology and protein chemistry. More specifically, the present invention relates to oncofetal antigen specific T-lymphocyte subclass mediated immune responses: manipulation and uses of oncofetal antigen specific CD4, CD8 cytotoxic and suppressor T cells and interleukin-10 for early cancer detection tests, for conventional therapy monitoring, and for immune-intervention through autologous T-cell therapy and anti-cancer vaccination.

2. Description of the Related Art

Established tumors can grow and kill the host bearing such tumors even though lymphocytes obtained from that host animal can adoptively transfer tumor immunity to other syngeneic animals (1–3). Also, investigators have shown that a tumor-bearing animal can reject challenge with part of that tumor when inoculated with tumor cells at a different site on its body (1, 4). This phenomenon has been termed concomitant immunity (2–4). Tumors can evade tumor-reactive lymphocyte-mediated destruction b y inhibiting protective immune responses directly, by secretion of inhibitory cytokines, and indirectly, by activating inhibitory regulatory elements of the immune system (5–11).

It has been suggested that rodents, like humans, challenged with carcinogens such as DNA-altering chemicals, radiation or oncogenic viruses respond as either "progressors", which develop advanced lethal tumors and die or "regressors", which fail to develop the fully malignant tumor cells giving rise to cancer. The "regressors" immunologically manage to control the tumor's growth or existence. These protective immune mechanisms at work in the regressors are widely believed to occur through cell-mediated responses mediated by a T-cell subclass, termed CD8 T-Cytotoxic or TC cells, and/or assisted by other antigen-specific T-lymphocyte subclasses including CD4 T-Helper 1 or TH-1 subclasses.

Approximately 60% of RFM mice develop lethal thymic lymphomas during a six month period subsequent to fractionated, sub-lethal X-irradiation (12,13). Systematic sampling of thymocytes of the irradiated mice during the first six months post-irradiation using intrathymic challenge assay into normal syngeneic mice revealed that when any $OFA^+$ thymocytes were transferred to normal thymus, a high correlation of adoptive induction of T-cell lymphoma was observed, suggesting that oncogenic cells were induced in all irradiated recipients by six months. However, only approximately half of the irradiated donor mice developed lymphomas. The irradiated mice that survive the first 6 months never show any physical signs of tumor development.

It has been shown that mice which had been irradiated 11 months previously and appeared tumor-free, had developed clonable memory CD4 and CD8 effector T cells which were specific for a 44 kDa oncofetal antigen (OFA) (14). It was also determined that age-matched, non-irradiated RFM mice yielded OFA-specific T cell clones; however the frequency of these T cell clones was significantly lower than the frequency in the long-term irradiation survivors, and the non-irradiated mice yielded no clones with high affinity anti-OFA T cell receptors. Immunobiology teaches that animals and humans which retain the capacity to respond to T or B-cell stimulating immunogens retain low affinity precursors and are able to respond to such non-self. Thus it is not surprising that such OFA-reactive memory T cells would be induced in the irradiated mice, since $OFA^+$ thymus cells are detectable as early as 2 weeks after irradiation but are entirely absent from non-irradiated, normal RFM/UnCr mice (13, 15).

However, even with these memory effector T cells that are tumor-reactive, challenge of previously-irradiated mice yielded no increased resistance to RFM lymphoma cells. In fact, such previously-irradiated mice showed significantly enhanced tumor growth kinetics compared to non-irradiated, age-matched controls that were challenged with the same tumor cells (14). This is likely because the previously-irradiated, long-term survivor mice had not only effector T cells, but also $CD8^+$ non-cytotoxic T cells that did not secrete interferon-γ. These non-cytotoxic CD8 T cells must secrete some factor(s) which inhibits the cytotoxic activity of anti-OFA cytotoxic T cell clones but does not inhibit $T_c$ clone cell proliferation (14).

All modern summaries of tumor immunobiology from other laboratories, attempting to characterize a host's immune response to emerging antigenic cancers (e.g., references 48–52), focus on the means by which the primary tumors and metastases "escape" the host's various humoral and cellular-mediated immune responses directed against the tumor. The focus has been instead on unshared, individual tumor specific transplantation antigen (TSTA). Rarely is a shared, host-cell encoded, tumor associated transplantation antigen (TATA) mentioned as the target for the specificity of these immune response. However, the focus of the present invention is on the 44 kD oncofetal antigen (44 kD OFA). OFA is an antigen which is normally expressed in embryonic and fetal tissue as phase-specific, developmentally regulated, embryonic antigen. The experiments leading to the present invention demonstrate, via flow cytometry and binding studies with anti-OFA monoclonal antibodies, that 44 kD OFA is distributed widely on all tumors of rodents and humans as a tumor-specific, but not a tumor subclass-specific, antigen or immunogen (see, e.g., refs 54–67). Since human cancers generally express 44 kD OFA, they too stimulate similar T-cell subclasses. Thus, identification of these anti-OFA responses in humans and animals during the development of cancer is used in the methods of the present invention to detect tumor presence and host mediated T-cell immune responses to emerging cancers using (a) peripheral blood lymphocytes (PBLs) of cancer patients as a source of OFA-specific precursors, (b) allogeneic or xenogeneic 44 kD OFA as a source of 44 kD OFA, and (c) autologous antigen processing cells to process the OFA for stimulation.

The prior art is deficient in effective means for screening individuals for shared oncofetal antigen (OFA) expression during early stage carcinoma and/or leukemia or lymphoma development. In addition, the prior art is deficient in effective means for monitoring a patient's immune response to oncofetal antigen (OFA) during treatment of the cancer. The present invention fulfills this longstanding need and desire in the art.

SUMMARY OF THE INVENTION

The present invention discloses that the inhibitory substance secreted by the non-cytotoxic CD8 T cell clones can inhibit T cell secretion of interferon-γ, is not antigen-specific, and is not MHC-restricted. The inhibitory substance, however, is neutralized by anti-IL-10 monoclonal antibody but not by an isotype control antibody. Also, the supernatants of these antigen-restimulated, non-cytotoxic CD8 T cells contain IL-10, while the supernatants of antigen-restimulated, cytotoxic CD8 T cell clones do not. The present invention thus also discloses that inclusion of anti-IL-10 antibody in the cultures of the non-cytotoxic CD8 T cell clones, rescues their anti-tumor cytotoxic ability. Further, it is shown that the IL-10 does not come from macrophages or tumor cells, but from the clones. Macrophages are not the targets of the inhibitory activity, but appear to act on the $T_c$ clone cells. Thus, the present invention demonstrates that CD8 T cells take on the functional activity of "suppressor" T cells for cell-mediated immunity by having the gene for IL-10 activated and the secretion of that cytokine can mask the functional potential of the secreting T cell itself.

It has been reported that in irradiated, long-term surviving RFM mice there is enhanced kinetics of tumor development upon challenge with RFM lymphoma cells. Splenic OFA-specific, non-cytotoxic, CD8$^+$ T cells from such mice were cloned. Upon antigen stimulation, these non-cytotoxic CD8$^+$ T cell clones secrete a factor that inhibits the ability of OFA-specific RFM $T_c$ cell clones from killing 5T RFM lymphoma cells in vitro. The supernatants from non-cytotoxic, CD8$^+$ T cells do not inhibit the tumor cell-induced proliferation of the $T_c$ cell clones, however. The present invention demonstrates that OFA-stimulated, non-cytotoxic, CD8 T cell clone culture supernatants also inhibit interferon-γ secretion by stimulated CD4 and CD8 anti-OFA effector T cell clones in a dose-dependent manner. The inhibitor in those culture supernatants acts neither in an antigen-specific nor MHC-restricted manner. OFA-stimulated non-cytotoxic CD8 T cell clones' culture supernatants contain IL-10, while those from OFA-stimulated, RFM OFA-specific $T_c$ clones do not. Moreover, the monoclonal anti-IL-10 antibody specifically blocks the inhibition of cytotoxic activity and interferon-γ secretion by OFA-specific CD8 and CD4 effector T cell clones in a dose-dependent manner in vitro. Incorporation of anti-IL-10 antibody into the cytotoxicity assays of the OFA-specific, non-cytotoxic CD8$^+$ T cell clones against 5T tumor cells restores their cytotoxic activity.

In one embodiment of the present invention, there is provided a method of determining the success of a cancer therapy in an individual, comprising the step of measuring the amount and frequency of oncofetal antigen-specific T-Cell subsets in the individual's peripheral blood lymphocytes (PBLs) or in tumor infiltrating lymphocytes (TILS) at the residual tumor site.

In another embodiment of the present invention, there is provided a method of determining whether protective immunity against a tumor will develop in an individual, comprising the step of measuring the frequency of oncofetal antigen-specific T cells which secrete IL-10 at the site of the tumor.

In yet another embodiment of the present invention, there is provided a method of determining the potency of the protective anti-tumor immunity in an individual, and the phenotype and composition of the T-cell subclasses involved, comprising the step of measuring the frequency of interferon-γ secreting T cells and oncofetal antigen-specific T cells at the site of the tumor.

The present invention is drawn to a method of stimulating and causing clonal expansion of memory CD4 helper cells, CD8 Tc cytoxic lymphocytes and CD8 non-cytotoxic T-suppressor lymphocytes comprising administering an effective dose of purified 44 kDa oncofetal antigen. Further, the present invention is drawn to a method for activating T-suppressor cells comprising inhibiting or limiting IL-10 production of said cells.

An additional method provided in the present invention is a method of screening an individual for early stage carcinoma, lymphoma development comprising: cloning oncofetal antigen specific T-cells from said individual; and determining a frequency of cytoxic T-cells and inhibitory T-suppressor cells that cause specific suppression of CD8 and CD4 cytoxicity.

In addition, the present invention provides a method for monitoring succes of cancer therapy and determining whether protective immunity will develop in an individual, comprising the step of measuring a frequency of oncofetal antigen-specific T cell subclasses, including CD8 cytotoxic T-cells and T-cells making IL-10, in said individual, wherein when said frequency of CD8 cytoxic T-cells is high and said frequency of T-cells making IL-10 is low, therapy is successful and development of protective immunity is likely.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention are attained and can be understood in detail, more particular descriptions of the invention may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows that the culture supernatants from non-cytotoxic, anti-OFA, CD8 T cell clones inhibit interferon-γ secretion by anti-OFA CD4 and CD8 T cell clones. The data are presented as mean IFN-γ concentration (pg/ml)±SEM. Experiments were repeated 3 times.

FIG. 2 shows the inhibitory activity of culture supernatants from non-cytotoxic CD8, anti-OFA T cell clones for IFN-γ secretion is not antigen-specific. The data are presented as mean IFN-γ concentration (pg/ml)±SEM. Experiments were repeated 3 times.

FIG. 3B shows the effect on IFN-γ secretion by BALB/c OFA-specific CD4 T cell clone 5 after preincubation with various amounts of culture supernatant collected from RFM non-cytotoxic T cell clones 9, 10, and 11 or from $T_c$ clone 4 one week after restimulation of those clones as described in FIG. 3A.

DETAILED DESCRIPTION OF THE INVENTION

Figure 1A:
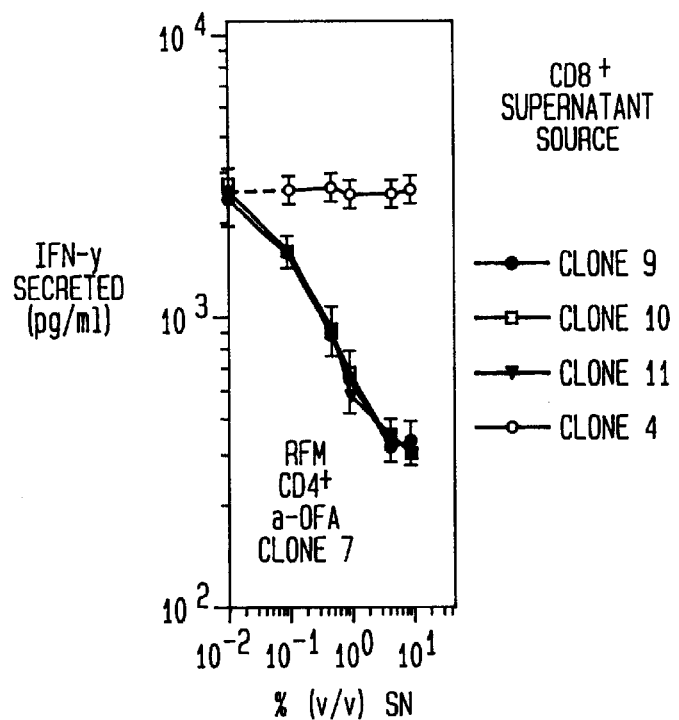
FIG. 1A shows the effect on IFN-γ secretion by anti-OFA CD4 T cell clone 7 after preincubation for 24 hours with various amounts of culture supernatant collected from non-cytotoxic T cell clones 9, 10, and 11 or from $T_c$ clone 4 one week after restimulation of the CD8$^+$ clones with irradiated RFM 5T lymphoma cells+irradiated RFM T cell-depleted spleen cells+recombinant murine IL-2.

It will be apparent to one skilled in the art that various substitutions and modifications may be made to the invention disclosed herein without departing from the scope and spirit of the invention.

As used herein, the term "oncofetal antigen" or "OFA" refers to an antigen which is normally expressed in embryonic and fetal tissue as phase-specific, developmentally regulated, embryonic antigen. A 44-kD OFA-associated polypeptide is obtained from membrane extracts of fetal cells and tumor tissues of humans and rodents (species conserved) by monoclonal antibody capture. These OFAs are also capable of eliciting a T cell immune response.

As used herein, the term "tumor-specific transplantation antigen" or "TSTA" refers to individually specific noncross-protective tumor specific transplantation antigens.

As used herein, the term "tumor-associated transplantation antigen" or "TATA" refers to cross-protective tumor associated transplantation antigens. For example, oncofetal antigen TATA is found in tumors of chemically-, virally- or radiation-induced tumors of rodents and man.

As used herein the term "CD4 effector cells" refers to a subset of T cells which are associated with cell-mediated immune response. They are characterized by the secretion profiles and IFN-γ.

As used herein the term "CD8 effector cells" refers to a subset of T cells which express CD8 on their surface, are MHC class I-restricted, and function as cytotoxic T cells.

As used herein the term "OFA-specific T cell clones" refers to clones which are stimulated to proliferate by recognition of OFA peptide(s) bound to syngeneic MHC class I or class II proteins on the surface of antigen-presenting cells. These clones also are induced to secrete gamma-interferon, IL-2, and in some cases IL-10 upon recognition of OFA peptide(s) presented to them on MHC class I or class II proteins on syngeneic antigen presenting cells.

As used herein the term "anti-OFA T cell receptors" refers to the αβ or γδ T cell receptors which specifically recognize OFA peptide(s) associated with syngeneic class I or class II MHC proteins.

As used herein the term "non-cytotoxic CD8$^+$ T cell" refers to CD8-expressing T lymphocytes which recognize and are stimulated to proliferate by some tumor antigen (e.g, OFA) peptide(s) presented by class I MRC proteins on the tumor cell, but cannot kill the tumor cells with which they interact. In some cases, this is because they secrete Interleukin 10 which inhibits their cytotoxic activity.

As used herein the term "cytotoxic CD8 T cell" refers to CD8-expressing T lymphocytes which recognize and are stimulated to proliferate by some tumor antigen (e.g, OFA) peptide(s) presented b y class I MHC proteins on the tumor cell. These CD8 T cells kill the tumor cells with which they interact, but can be inhibited from doing so by exogenous IL-10.

As used herein the term "peripheral blood lymphocytes" or "PBLs" refers to lymphocytes in an animal's circulating blood.

As used herein the term "tumor inflitrating lymphocytes" or "TILs" refers to lymphocytes found within and around a tumor which presumably recognize some tumor antigen or peptides of it combined with class I or class II MHC proteins on the tumor cell. They are part of an immune response against the tumor, but some those TILs may be inhibitory to potentially protective immune responses Some are CD4 and CD8 effector cells.

As used herein the term "antigen processing cells" refers to cells which take up proteins and process them into small peptides (8–9 amino acids) to be presented to T cells via the major histocompatibility molecules.

As used herein the term "intrathymic challenge assay" refers to an assay for thymoma pretumor cells in which subsequent to fractionated, sublethal, whole-body X-irradiation, graded doses of thymus cells from one strain of mouse are injected into the thymus of nonirradiated congenic mice which differ only in a T lymphocyte marker allele. Thus, thymic tumors that develop can be tested for that T cell marker allele to determine if the tumor arose from the donor thymocytes or from the recipient mouse thymocytes. By giving graded doses, one can determine the number of pre-malignant thymocytes in the donor thymus.

As used herein the term "RFM/UnCr mice" refers to a strain of mice bred at Charles Rivers Breeding Laboratories that have the H-2f MHC genotype, are albino, and which develop thymic lymphoma/leukemia subsequent to fractionated, sublethal whole-body X-irradiation. RFM is the strain name.

As used herein the term "5T" refers to the radiation-induced Lymphoblastic Lymphoma cell line XR11-5T isolated from the thymus of RF/M mouse. This cell line is of thymic origin and L3T4$^+$, Lyt-2$^+$, and Thy-1$^+$.

As used herein the term "IFN-γ" refers to an abbreviation for gamma interferon (or interferon-γ). Gamna interferon is a cytokine produced and secreted by activated T lymphocytes. It can protect cells from becoming infected with virus. It also can enhance MHC class I and II expression on B lymphocytes and macrophages, and at higher levels induces class II on many tissue cells to enhance antigen presentation. It increases IL-2 receptors on cytotoxic T lymphocytes, enhances cytotoxic activity of large granular lymphocytes and promotes B cell differentiation to IgG-producing cells. Gamma interferon is the principle cytokine responsible for macrophage arming factor activity which increases macrophage $F_c$ receptor expression on macrophages as well as inducing the macrophages' respiratory burst, thereby enhancing their ability to kill infecting microbes as well as tumor cells. It can inhibit proliferation of Th2 CD4 T cells (T helper cells for antibody production). It is a marker cytokine for the CD4 effector T cells.

As used herein the term "IL-10" refers to a cytokine produced by a number of cell types including T lymphocytes and macrophages. Interleukin-10 can promote the growth and activation of some immune cells, but it is secreted by CD4 Th2 cells and inhibits activation of Th1 cells and especially inhibits their secretion of gamma interferon. It acts mostly through antigen-presenting cell inhibition, but the inventors of the present invention have shown that it inhibits antitumor cytotoxic T cell activity directly.

As used herein the term "$T_c$ clone cell" refers to T lymphocytes which have been cloned from peripheral blood, spleen, lymph node, or from tumor-infiltrating lymphocytes. A clone of this type is cytotoxic for tumor cells and usually expresses CD8 and recognizes some tumor antigen peptide bound to autologous (or syngeneic) class I MHC proteins. It is specific in its killing in that it only kills those cells which express the tumor antigen peptide(s) on the tumor cells' class I MHC molecules. In the studies developing the present invention, they also secrete gamma interferon upon stimulation by the tumor cells or the tumor cell antigen peptide(s).

As used herein the term "MCA1315" refers to fibrosarcoma cells induced into the tumorigenic state by subcutaneous injection of BALB/c mice with methylcholanthrene (MCA). Tumor cell lines are then isolated and the different isolates are given serial numbers.

As used herein the term "IMDM" refers to Iscove's Modified Dulbecco's Medium.

As used herein the term "ELISA" refers to the Enzyme Linked Immunosorption Assay.

The use and methods of preparation of oncofetal antigen or oncofetal antigen specific monoclonal antibodies has been disclosed in U.S. Pat. No. 4,686,180 for human and animal cancer detection, therapy, and therapy monitoring. A 44 kDa oncofetal antigen glycoprotein (gp) and a 200 kDa glycoprotein, possibly containing the 44 kDa component, have been shown to be a species-conserved, cell surface associated glycoprotein which serve as embryo/fetal and cancer specific antigens and immunogens in inbred pregnancy and in primary rodent cancer models. Oncofetal antigens are present in early and mid-gestation rodent and human fetus and are consistently re-expressed in tumor tissue, but are not present in normal term, neonate, or adult tissues.

Oncofetal antigen serves as a Tumor Associated Transplantation Antigen (TATA) in rodent cancer systems representive of all three germ lines giving rise to adult tissues and tumors. Oncofetal antigen in crude or purified form, as identified with oncofetal antigen-specific monoclonal antibodies and OFA-specific T-cells, can promote both B-cell mediated anti-oncofetal antigen antibody production as well as protective, T-cell mediated immunity in syngeneic rodents.

Human lung cancer patients appear to make IgG to oncofetal antigen that is present in the tumors. The antibody was detected by an ELISA absorption procedure with fresh autologous biopsy material or purified mouse or human oncofetal antigen. Oncofetal antigen, delivered in an appropriate dosage and frequency for vaccination, can promote tumor immunity to challenge, as well as prevent the induction of primary tumors in rodents. Oncofetal antigen on fetal cells has been conferred to interrupt chemical carcinogenesis in rats and viral carcinomas in hamsters when used as vaccine. T-cell mediated immune responses are credited with oncofetal antigen associated tumor protection.

The 44 kDa oncofetal antigen prepared in purified form can stimulate and cause the clonal expansion of memory CD4 helper (Th1) and CD8 $T_c$ cytotoxic lymphocytes as well as CD8 non-cytotoxic (Ts) T-suppressor lymphocytes in inbred mice experiencing and subsequently eliminating X-ray-induced lymphomagenesis or 3-MCA sarcoma production. These mice were never presented with oncofetal antigen via direct immunization. The mice immunologically "experienced" oncofetal antigen re-expressed and present on their own primary tumors after or during malignant transformation. The mice were nevertheless sensitized to the oncofetal antigen on their primary tumors and were found to carry oncofetal antigen specific T-cells that could be clonally expanded when stimulated with purified syngeneic or allogeneic mouse oncofetal antigen in culture medium containing specific supplements. 44 kDa oncofetal antigen, in the presence of selected cytokines, stimulates the enrichment of these clones in vitro. Highly stable CD4 and CD8 T-cell clones were thus derived and exhaustively tested for function in vitro. The clones selected as oncofetal antigen specific could functionally "help" as CD4 cells in tumor cell destruction by arousing macrophages or by stimulating expansion of CD8 protective effector cells which could kill autologous tumor target cells in vitro. Other CD8 clones that arose were not cytotoxic but could ablate CD8 T-cell mediated oncofetal antigen TATA or TSTA specific cytotoxicity in response to the expression of oncofetal antigen on primary X-ray or MCA sarcoma tumor cells. Thus, OFA specific T-cell subclasses are useful in predicting tumor destruction or promotion in vivo.

Taken together, the findings regarding B-cells and T-cells demonstrate that reliable tests can be devised to screen humans for oncofetal antigen expression in early stage carcinoma and/or leukemia or lymphoma development. Immune cells from individuals may be tested for oncofetal antigen specificity to the individual's own tumor's expression of the TATA to predict tumor prognosis based on analysis of autologous immune reactions. The status of an individuals's cancer progression and host cell mediated resistance to an individual's cancer may also be predicted, because oncofetal antigen specific T-cells can be cloned and the frequency of protective, cytotoxic T-cells and also inhibitory Ts-cells that cause specific suppression of CD8 and CD4 cytotoxicity in the tumor site [TILs] or in peripheral blood of the individual can be quantitated.

The cytokine IL-10 has been identified as primarily responsible for this suppressor effect. CD8 secreted by the Ts cell clones cytotoxic cells can now be phenotypically distinguished from CD8 Ts by whether they make IL-10. Therapeutically, Ts-cell clones may be used and altered into regaining killing potential for tumor target cells by inhibiting or limiting the IL-10 production in the cells. All the above technology with T-cells can be accomplished using peripheral blood lymphocytes and/or tumor infiltrating lymphocytes (TILs) and the purified 44 kDa oncofetal antigen glycoprotein using cloning and enumeration techniques developed in mice as well as cultured splenocytes. Human and rodent cancers presented essentially identical 44 kDa molecules. Early protein peptide sequencing evidence indicated that oncofetal antigen may be related to a surface glycoprotein which has been partially characterized as an invasive non-integrin-associated 68 kDa laminin binding protein (LPB) which contains a 44 kDa component and a 18–25 kDa component LPB, in modified form may enable tumor cells to invade and penetrate endothelial lining of blood vessels. The oncofetal antigen product may, in part, be an altered or abnormally-expressed normal cell binding molecule, present in different form in fetal and tumor cells.

There are many uses of monitoring oncofetal antigen-specific T cell subclasses or IL-10 or interferon-γ of the present invention that are specfically contemplated. For example, the present invention is directed to a method of determining whether protective immunity against a tumor will develop in an individual, comprising the step of measuring the frequency of oncofetal antigen-specific T cells, at the site of the tumor and/or in peripheral blood; and further directed to a method of determining the potency of the protective anti-tumor immunity, comprising the step of measuring the frequency of interferon-γ secreting T cells and oncofetal antigen-specific T cells at the site of the tumor. The present invention is also directed to a method of determining whether an individual having a tumor will go into remission or remain in remission, comprising the step of measuring the frequency of oncofetal antigen-specific Th1 cells, Tc cells and Ts cells, IL-10 and interferon-γ secreting T cells in the peripheral blood of the individual.

In one embodiment, the present invention is directed to a method of predicting and monitoring the success of a cancer therapy in an individual, comprising the step of measuring the frequency or numbers of oncofetal antigen-specific subclasses in the individual's peripheral blood. More specifically, the present invention is directed to a method of determining the success of a cancer therapy in an individual, comprising the step of measuring the frequency of OFA-specific Th1 cells, Tc cells, and Ts cells and/or cytokines in peripheral blood or tumor infiltrating lymphocytes.

One aspect of the present invention is directed to a straightforward assay to predict remission mediated by OFA and TSTA-specific CD8+ $T_c$ cells. The assay measures the number of CD8+ cytotoxic T-cell subclasses and peripheral blood lymphocyte T-cell clones making IL-10, after stimulation by purified 44 kD OFA, in individuals. After post-surgical debulking of the primary tumor or other cancer therapy, patients expressing substantial numbers of CD8+ cytotoxic T-cell subclasses, and containing few or no peripheral blood lymphocyte T-cell clones making IL-10, after stimulation by purified 44 kD OFA, would be considered to be in remission. In addition, CD4 Th1 cells may also be measured as they contribute to either direct or recruited tumor resistance, once they have been stimulated by 44 kD OFA.

On the other hand, patients with progressive disease are not expected to have OFA specific competent CD8+ Tc cell subclasses or functional TSTA-specific subclasses when IL-10-secreting Tc-cells are present in significant numbers. The in vitro cytotoxicity of CD8+ T-cell clones expanded by purified or recombinant OFA may be tested in vitro to determine whether CD8+ clones can kill tumor cells in vitro, particularly carcinomas of all types. The 44 kD OFA restimulates native tumor-sensitized Tc CD8 cells in patients whose prognosis is good for remission.

Kits directed to the convenient practice of this embodiment of the present invention contain the control lymphokines (IL-2, IL-6) for culturing the Tc subclasses; purified or recombinant 44 kD OFA from human or rodent sources which are shared by the carcinoma for stimulating the expression of T-cell clones specific for OFA or TATA. Control reagents include but are not limited to cell fractions from human cells not expressing OFA or TATA.

It is specifically contemplated that the methods for measuring the progress of cancer therapy, detecting cancer at an early stage, and determining the existence and potency of protective immunity described above may be performed easily with a kit. Such a kit would test a patient's PBLs or TILs for frequency of OAF CD8+ Tc and CD4 Th1 cells, and may contain the following components:

IL-2, IL-6 for growth promotion of clones, reagents for typing cytokines made by these T-cell subclasses medium for clonal expansion of PBLs and for separation memory or precursor T-cells to be stimulated in vitro;

medium for culturing autologous tumor cells;

Purified 44 kD OFA on nitrocellulose for stimulation of OFA specific Tcell subclasses;

control "antigens" for stimulation specify (non-OFA containing control tissue components less OFA), and r-37-OFA [LBP];

reagents to prepare semi-purified OFA from cultured, autologous human cells;

medium for isolating PBL APCs;

DNA stimulation assay reagents; and

CD4 and CD8 phenotyping reagents for CD4 and CD8 functioning cells.

In addition, the presence of IL-10 or IL-10 mRNA in CD8+ T cells, detected with two and three color fluorescence in fixed and permeabilized T-cell flow cytometry using either in peripheral blood lymphocytes or in tumor inflitrating lymphocytes in the tissues of the residual tumor bed, indicates a strong potential for tumor promotion and cancer regrowth. Thus, detecting IL-10 levels in culture supernatants of clonally expanded T-cells or in tumor infiltrating lymphocyte-containing biopsy tissues taken from the tumor bed is an additional assay for monitoring the progression of disease or the effectiveness of therapy. A kit for this method of measuring IL-10 levels would include: Mab to IL-10 or probes specific for detecting mRNA for IL-10

The present invention is also directed to methods of quantitation of TH1 cells associated cytokines (for example IL-2, INF-γ) and TH2 cells associated cytokines (for example IL-4, IL-10) protein and mRNA in peripheral blood.

Thus, the present invention specifically is drawn to a method of stimulating and causing clonal expansion of memory CD4 helper cells, CD8 Tc cytotoxic lymphocytes and CD8 non-cytotoxic T-suppressor lymphocytes comprising administering an effective dose of purified 44 kDa oncofetal antigen. Further, the present invention is drawn to a method for activating T-suppressor cells comprising inhibiting or limiting IL-10 production of said cells.

It is specifically contemplated that pharmaceutical compositions may be prepared using the purified 44 kDa oncofetal antigen of the present invention. In such a case, the pharmaceutical composition comprises the the purified 44 kDa oncofetal antigen of the present invention and a pharmaceutically acceptable carrier. A person having ordinary skill in this art would readily be able to determine, without undue experimentation, the appropriate dosages and routes of administration of the the purified 44 kDa oncofetal antigen of the present invention. When used in vivo for therapy, the purified 44 kDa oncofetal antigen of the present invention is administered to the patient or an animal in therapeutically effective amounts, i.e., amounts that eliminate or reduce the tumor burden. It will normally be administered parenterally, preferably intravenously, but other routes of administration will be used as appropriate. The dose and dosage regimen will depend upon the nature of the cancer (primary or metastatic) and its population, the characteristics of the particular immunotoxin, e.g., its therapeutic index, the patient, the patient's history and other factors. The amount of purified 44 kDa oncofetal antigen administered will typically be in the range of about 0.1 to about 10 mg/kg of patient weight. The schedule will be continued to optimize effectiveness while balanced against negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press; which are incorporated herein by reference.

For parenteral administration the protein will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The purified 44 kDa oncofetal antigen will typically be formulated in such vehicles at concentrations of about 0.1 mg ml to 10 mg ml.

An additional method provided in the present invention is a method of screening an individual for early stage carcinoma, lymphoma development comprising: cloning oncofetal antigen specific T-cells from said individual; and determining a frequency of cytoxic T-cells and inhibitory T-suppressor cells that cause specific suppression of CD8 and CD4 cytotoxicity.

In addition, the present invention provides a method for monitoring succes of cancer therapy and determining whether protective immunity will develop in an individual, comprising the step of measuring a frequency of oncofetal antigen-specific T cell subclasses, including CD8 cytotoxic T-cells and T-cells making IL-10, in said individual, wherein when said frequency of CD8 cytoxic T-cells is high and said frequency of T-cells making IL-10 is low, therapy is successful and development of protective immunity is likely.

The following examples are given for the purpose of illustrating various embodiments of the invention and are not meant to limit the present invention in any fashion.

EXAMPLE 1

Mice

RFM/UnCR male and female 6–10 week old mice used in these experiments were obtained through NIH from Charles Rivers Breeding Laboratories (Wilmington, Mass.).

EXAMPLE 2

Tumor Cells

The RFM thymic lymphoma 5T used for restimulation of clone proliferation (13) was cultured in Iscove's Modified Dulbecco's Medium (IMDM) supplemented with 100 U/ml Penicillin G and 100 μg/ml Streptomycin sulfate, 10% control process serum replacement 3 (CPSR-3) (Sigma Chemical Company, St. Louis, Mo.), 2 mM L-glutamine, and 3.024 g/L sodium bicarbonate. The cells were maintained in a 37° C. humidified 5% $CO_2$, 95% air atmosphere. The BALB/c fibrosarcoma MCA1315 which was used to restimulate BALB/c anti-oncofetal antigen clones was cultured in the same medium under the same temperature-$CO_2$ conditions.

EXAMPLE 3

Cell Lines

The gibbon T cell lymphoma MLA-144 (American Type Culture Collection, Rockville, Md.) constitutively secretes gibbon IL-2 (16), and was cultured in IMDM supplemented with $7.5 \times 10^{-5}$ M α-thioglycerol, 2 mM L-glutamine, sodium bicarbonate (3.024 g/L), 100 U/ml Penicillin G, 100 μg/ml Streptomycin sulfate, and 10% CPSR-3 (Sigma Chemical Company, St. Louis, Mo.) (complete IMDM).

EXAMPLE 4

Monoclonal Antibodies

Rat monoclonal anti-mouse IL-10 IgM antibody (clone AB-71-005) and rat monoclonal anti-mouse CD11b (Mac-1) (clone M1/70) were purchased from BioSource International (Camarillo, Calif.). Normal rat IgG which was used as a control isotype antibody was purchased from Pharmingen (San Diego, Calif.). Rat monoclonal anti-mouse B220 IgM antibody was purified by ammonium sulfate precipitation and Sephadex G-200 gel filtration from culture supernatants of hybridoma RA3-3A1/6.1. Rat monoclonal anti-mouse CD4 antibody (hybridoma GK1.5) and rat monoclonal anti-mouse CD8 antibody (hybridoma 53–6.72) were purified by ammonium sulfate precipitation and protein G affinity chromatography from culture supernatants. These hybridomas were obtained from the American Type Culture Collection (Rockville, Md.) and maintained in the laboratory.

EXAMPLE 5

T Cell Clone Maintenance

The clones were cultured in sterile IMDM supplemented not only with 100 U/ml of recombinant murine IL-2 and 100 U/ml of recombinant murine IFN-γ, but also with 10 U/ml of recombinant murine IL-6. Sterile filtered MLA-144 culture supernatant was used as the source of IL-2 (at 25% v/v). The RFM clones were restimulated with irradiated 5T cells and the BALB/c clones were restimulated with irradiated MCA1315 cells every two weeks in the presence of irradiated syngeneic spleen cells and complete IMDM supplemented at 25% v/v final concentration with MLA-144 culture supernatant to maintain the clones' viability and proliferation.

EXAMPLE 6

Determination of T cell clones cytotoxic T cell activity against 5T lymphoma target cells Cytotoxicity assays were performed using the CytoTox 96 non-radioactive cytotoxicity assay kit produced by Promega (Fisher Scientific, Atlanta, Ga.). The assay quantitatively measures lactic dehydrogenase (LDH), a stable cytosolic enzyme that is released upon cell lysis. Released LDH in culture supernatants is measured with a 30 minutes coupled enzymatic assay resulting in the conversion of a tetrazolium salt to a red formazan product (18). The amount of color formed was proportional to the number of lysed cells. Color was quantitated using a Biotek ELISA reader measuring absorbance at T492 nm. Preliminary experiments determined that use of 10,000 viable 4T or 5T lymphoma cells would allow release of enough LDH upon lysis to give a strong absorbance. Each time a cytotoxicity assay was done, duplicate control wells containing only target cells, only effector cells, or only medium were run to control for spontaneous release of LDH by effector and target cells and for any color provided by the medium itself. Initially, all data had the medium control absorbance value subtracted from them. Duplicate wells containing only medium to which 10 μl of 10× lysis solution was added were used for a volume correction control. The average absorbance of that control was subtracted from the absorbance values obtained from the target cell maximum release wells. The percent specific cytotoxicity was calculated using the formula listed below:

$$\% \text{ Cytotoxicity} = \frac{(\text{Exp.} - \text{Effector Spontaneous}) - \text{Target Spontaneous}}{\text{Target Maximum} - \text{Target Spontaneous}} \times 100$$

This assay has much less spontaneous release of LDH than one gets of $^{51}$Cr in a traditional $^{51}$Cr release cytotoxicity assay and so higher specific cytotoxicity percents are achieved.

At the time of the two week restimulation of the clones to maintain their proliferation, the cloned cells were harvested, washed in IMDM, and a viability count was done. A portion of the cells was saved out to be used in the cytotoxicity assay. Into 8 wells of V-bottomed 96 well plates, were placed 200 μl of medium-washed target 5T lymphoma cells such that there were 10,000 cells/well in the target spontaneous release control and the target maximal release control wells. Into 6 wells/clone of V-bottomed 96 well plates were placed 100 μl of medium-washed target 5T lymphoma cells such that there were 10,000 live target cells/well. Into each of two wells/clone was added 100 μl of medium-washed cloned T cells at 12.5 clone cells:1 target cell, 25 clone cells:1 target cells, or 50 clone cells: 1 target cell. These are the experimental wells. Into 6 wells/clone were placed 200 μl of medium-washed cloned T cells at the same concentrations as in the experimental wells except that no target cells are present. These serve as the effector spontaneous release wells. The 96 well plates were centrifuged at 250 ×g for 4 minutes to pellet all cells and then incubated for 4 hours at 37° C. in a humidified, 95% air/5% $CO_2$ atmosphere. At the end of this incubation, 10 μl of 10× lysis solution/100 μl of medium was added to each of the maximal release wells to lyse the targets. The plates were then continued to be incubated at 37° C. for another 45 minutes. The plates were then centrifuged at 250×g for 4 minutes to pellet remaining cells and 50 μl of culture supernatant from all wells was transferred to a flat-bottomed 96 well ELISA plate. 50 μl of reconstituted substrate mix in assay buffer was then added to each well and the plates were incubated at room temperature for 30 minutes. This substrate solution contained lactate, NAD (nicotinamide-adenine dinucleotide), INT(p-idonitrotetrazolium violet chloride), tetrazolium salt, and the enzyme diaphorase at optimal concentrations for these volumes. 50 μl of stop solution was added to each well, any bubbles were removed and the absorbance at 492 nm wavelength was determined using a Biotek ELISA reader.

EXAMPLE 7
Determination of inhibitory activity of supernatants from non-cytotoxic CD8+T cell clones on interferon-γ secretion One day before the required every two week re-exposure of the clones to irradiated 5T tumor cells in the presence of irradiated spleen cells and IL-2, some of the cells from the clones to be tested were harvested, washed three times in IMDM, and viability counts were performed. The cells were seeded into 24 well plates at $10^5$ viable cells/ml in IMDM containing IL-2±various amounts of culture supernatant taken from non-cytotoxic CD8+ clones or from cytotoxic clone 4. The culture supernatants used were obtained one week after re-stimulation with irradiated 5T tumor cells in the presence of irradiated T cell-depleted RFM spleen cells+IL-2. The cytotoxic clones were incubated±the supernatants for 24 hours and then harvested, washed three times in IMDM and counted for viability. The supernatant-treated clone cells were then restimulated by irradiated 5T lymphoma cells or MCA 1315 fibrosarcoma cells in the presence of irradiated T cell-depleted syngeneic spleen cells+IL-2 for 48 hours and the supernatants collected, sterilized by filtration and assayed for interferon-γ by ELISA.

EXAMPLE 8
ELISA determination of interferon-γ secretion by the T cell clones An interferon-γ assay kit from Genzyme Corp. (Cambridge, Mass.) was used. Briefly, a 96-well flat-bottomed ELISA plate was coated with monoclonal anti-mouse IFN-γ antibody in coating buffer (0.1 ml/well), the wells sealed with plastic sealant, and incubated overnight in a humidified box at 4° C. The coating solution was aspirated from the wells and each well washed with 200 μl of washing buffer followed by aspiration. This wash was repeated three times. The plate was then blotted dry and 200 μl of blocking/dilution buffer added to each well. The plate was sealed and incubated at 37° C. for 30 minutes. At the end of this incubation, the plate was unsealed and the liquid aspirated from the wells. The 100 μl of medium (negative control) was placed in two wells, 100 μl of recombinant IFN-γ (diluted in medium to 125 to 8200 pg/ml) placed in two wells/ concentration (standard curve), and 100 μl of each test sample was placed in two wells/sample. The plate was sealed and incubated at room temperature for 2 hours. After that incubation, the liquid was aspirated from the wells and each well was washed four times with washing buffer at room temperature and the plate blotted dry.

The 100 μl of diluted polyclonal goat anti-mouse IFN-γ antibody was then added to each well and the plate sealed and incubated for 2 hours at room temperature. The liquid was then aspirated from the plate and the plate washed four times with washing buffer and blotted dry. The 100 μl of diluted polyclonal donkey anti-goat Ig antibody that was conjugated with horseradish peroxidase was added to each well, the plate sealed, and incubated at room temperature for 1 hour. The liquid was aspirated from the plate and the plate was washed four times with washing buffer then blotted dry and 100 μl of diluted substrate reagent (OPD chromogen in substrate reagent buffer/eroxide solution) was added to each well. The plate was incubated at room temperature until a faint yellow color was discernible in wells containing 125 pg/ml mouse IFN-γ, which was usually 4 to 6 minutes. At that point, 100 μl of 2 N sulfuric acid was added to each well in the same order as the substrate reagent was added to stop the reaction. The plate was then read in a Biotek ELISA reader measuring absorbance at 492 nm. The average absorbance reading of duplicate wells was determined and the average absorbance of the negative control subtracted from all averages. The average absorbance for each concentration of IFN-γ used in the standards (on the y-axis) was plotted against the concentration of IFN-γ (on the x-axis) on semilog graph paper. The concentration of IFN-γ in the test culture supernatants was determined by using the stancard curve that is generated. The standard curve was linear between 250 and 4100 pg/ml.

EXAMPLE 9
ELISA determination of IL-10 secretion by the T cell clones

An IL-10 ELISA assay kit from Bio-Source International (Camarillo, Calif.) was used. Briefly, in a 96 well flat-bottomed ELISA plate coated with monoclonal anti-mouse IL-10 antibody was added 100 μl of the standard diluent to the blank and zero wells and 100 μl of standards, experimental supernatants, and controls were added to appropriate wells. The plate was covered and incubated for 1.5 hours in a 37° C. incubator. After that incubation, the liquid was aspirated from the wells and the wells washed 4× with wash buffer. The plate was then inverted and allowed to drain. To all wells except blank wells was then added 100 μl of biotinylated anti-IL-10 antibody. The plate was then covered and incubated at 37° C. for 45 minutes. The liquid was then aspirated and the wells washed 4× with wash buffer and drained. Following that, 100 μl of 1:100 diluted horseradish peroxidase (HRP)-conjugated Streptavidin solution was added to all wells. The plate was then covered and incubated at 37° C. for 45 minutes. The liquid was then aspirated and the wells washed 4× with wash buffer and drained. 100 μl of stabilized TMB chromogen was added to all wells and the plate covered and incubated at room temperature in the dark for 20 minutes. 100 μl of Stop Solution was then added to each well, gently mixed, and the absorbance at 450 nm determined for each well on a BioTek ELISA reader. The blank well contained only the chromogen and stop solution. All wells were done in duplicate. The average absorbance reading of duplicate wells was determined and the average absorbance of the negative control subtracted from all averages. The average absorbance for each concentration of IL-10 used in the standards (on the y-axis) was plotted against the concentration of IL-10 (on the x-axis) on semilog graph paper. The concentration of IL-10 in the test culture supernatants was determined by using the standard curve that was generated. The sensitivity of this ELISA was <13 pg IL-10/ml and the standard curve was linear between 31.2 pg/ml and 2000 pg/ml.

EXAMPLE 10
Ability of anti-IL-10 to block inhibitory supernatant effects on IFN-γ secretion and cytototoxicity by T cell clones One day before the two-week restimulation of the RFM T cell clones with 5T lymphoma cells, the cultures were harvested, washed thrice in IMDM and a portion of the cells counted for viability. $2 \times 10^5$ viable cells/ml were seeded into wells in a 24 well plate in IMDM+IL-2. Into most cultures was added culture supernatant from non-cytotoxic, oncofetal antigen-specific CD8 T cell clones 9, 10, or 11 or culture supernatant from cytotoxic CD8 T cell clone 4 to a final concentration of 10% (v/v). To this solution was added various concentrations of monoclonal anti-IL-10 or anti-B220 IgM antibodies and the cultures incubated at 37° C. for 24 hours. At the end of this incubation, the cells were harvested, washed thrice in medium, added to a restimulation culture as described previously (16) and 48 hours later supernatant was collected and assayed for IFN-γ. Determination of anti-IL-10 blocking of the inhibition of cytotoxicity was done the same way except that after the 24 hour incubation with inhibitory supernatant±anti-IL-10 antibody, the cells were harvested, washed, counted, and put in a cytotoxicity assay as described above.

EXAMPLE 11
Determination of anti-IL-10 conversion of non-cytotoxic CD8, oncofetal antigen-specific T cell clones to cytotoxic clones In order to determine if the clones that were secreting IL-10 were being inhibited by it, the cells were harvested one day before the two week restimulation culture and set up with 10 μg/ml anti-IL-10 IgM or anti-B220 IgM as described above for 24 hours. The cells were then harvested, washed thrice in IMDM, and viability counts performed. The cells were then added to an anti-5T cytotoxicity assay as described above, except that anti-IL-10 or anti-B220 was added to a final concentration of 10 μg/ml.

EXAMPLE 12
IL-10 produced by non-cytotoxic TCell:5Ttumor cell cultures during clone restimulation was not due to tumor cell IL-10 production One week after restimulation of cytotoxic and non-cytotoxic CD8 T cell clones with irradiated 5T cells, the cells were harvested, washed three times in IMDM and the tumor cells separated out by two serial positive selections on anti-mouse CD4-coated sterile bacterial Petri plates and two serial positive selections on anti-mouse CD8-coated plates. A modification of the method of Wysocki and Sato (18) was used in that the antibody was coated on the plates the day of cell separation. After non-adherent cells were gently washed away, sterile PBS was added and the plates agitated, followed by pipetting off the cells attached to the Petri plates. These cells were then washed three times in IMDM, viability counts done, and the tumor cells cultured for 48 hours in IMDM and culture supernatants collected, sterile filtered, and assayed for IL-10 as described above.

The T cell clones were separated from the tumor cells by a combination of negative selection using anti-CD4 antibody+facilitating antibody+low toxicity rabbit complement to remove CD4 T cells (including the 5T cells). The remaining cells were washed three times in IMDM, and positively selected on anti-CD8-coated Petri plates using a modification of the method of Wysocki and Sato (19) as described above. The extent of depletion and enrichment were determined by immunofluorescent microscopy analysis. The resulting CD4$^-$, CD8$^+$ T cells were cultured in IMDM+recombinant IL-2 for 48 hours and the supernatant was sterile filtered and assayed for IL-10 by ELISA. The 5T lymphoma cells and the T cell clones could be separated because the 5T tumor cells are CD4$^+$, CD8$^+$ T cells (12) while the clones are CD4$^-$, CD8$^+$ T cells (15).

EXAMPLE 13
Macrophages were neither the source nor the target of the IL-10

To show that macrophages, which were in the clone restimulation cultures, were not the source of the IL-10 subsequent to 5T restimulation of non-cytotoxic CD8 T cells, the T cell clone cultures were harvested 1 week after restimulation with irradiated 5T lymphoma cells+irradiated T cell-depleted spleen cells. The clone cells were serially negatively and positively selected for CD4 and CD8 as described above or the cells were treated with anti-CD11b+ anti-rat IgG antibody+low-toxicity rabbit complement to eliminate macrophages and the selected cell subpopulations separately were cultured for 48 hours in IMDM +recombinant IL-2. The culture supernatants were then harvested and sterile filtered. IL-10 was assayed by ELISA as described above.

Similarly, to determine that macrophages were not the target of the IL-10, anti-oncofetal antigen CD8$^+$ cytotoxic T cell clone 1 cultures were harvested one day before the required 5T restimulation of the clones and the cells washed three times in medium and treated with rat anti-mouse monoclonal CD11b antibody+anti-rat IgG+low toxicity rabbit complement (to eliminate macrophages) or with rat IgG isotype control antibody+anti-rat IgG+low toxicity rabbit complement. The remaining cells were washed three times with IMDM and treated for 24 hours with supernatants from non-cytotoxic clones 9, 10, or 11 or from cytotoxic T cell clone 4 as described previously (14). The clone cells were then assayed for anti-5T cytotoxicity as described above.

EXAMPLE 14
Statistical Analysis of Data

Most data were analyzed for significant differences using Student's t-test. The data from experiments in which dose response curves were generated were analyzed using Analysis of Variance. A p value<0.05 was considered significant.

Figure 1B:
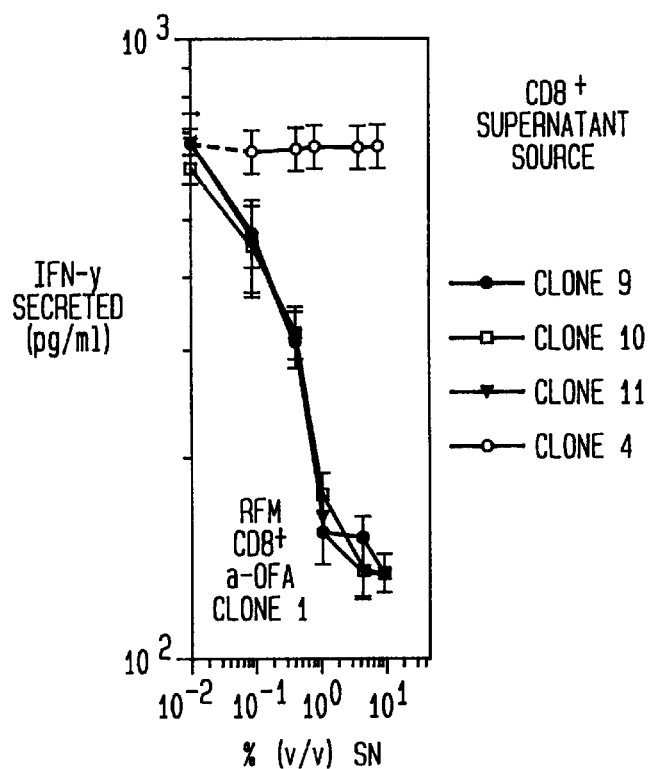
FIG. 1B shows the effect on secretion of IFN-γ anti-OFA CD8 $T_c$ cell clone 1 after preincubation with various amounts of culture supernatant from non-cytotoxic T cell clones 9, 10, and 11 or from $T_c$ clone 4 collected one week after restimulation of those CD8$^+$ clones as described in FIG. 1A above.

EXAMPLE 15
Supernatants from non-cytotoxic, anti-OFA CD8 T cell clones inhibit interferon-γ secretion by anti-OFA CD4 and CD8 T cell clones Supernatants from non-cytotoxic, CD8 T cell clones derived from long-term survivors of radiation carcinogenesis inhibit anti-oncofetal antigen cytotoxic T cell clone killing of syngeneic, oncofetal antigen$^+$5T lymphoma cells (14). The culture supernatants of three of these non-cytotoxic CD8 clones was assayed for their ability to inhibit the secretion of interferon-γ by the anti-oncofetal antigen CD4 T cell clone 7 and the anti-oncofetal antigen CD8 cytotoxic T ($T_c$) clone 1 subsequent to their restimulation b y irradiated 5T RFM lymphoma cells. The supernatant from oncofetal antigen-specific $T_c$ cell clone 4 was used as a negative control. Incubation for 24 hours in IMDM containing as much as 10% (v/v) final concentration supernatant from cytotoxic clone 4 had no inhibitory activity on the ability of either CD4 clone 7 (FIG. 1A) or cytotoxic CD8 clone 1 (FIG. 1B) to secrete interferon-γ after a 48 hour stimulation culture with irradiated RFM spleen cells±irradiated RFM 5T lymphoma cells. The supernatants from the three non-cytotoxic CD8 T cell clones, however, inhibited gamma interferon secretion in a dose-dependent manner with a 50% inhibition at 0.35–0.4% supernatant concentration (FIGS. 1A and 1B).

Figure 2A:
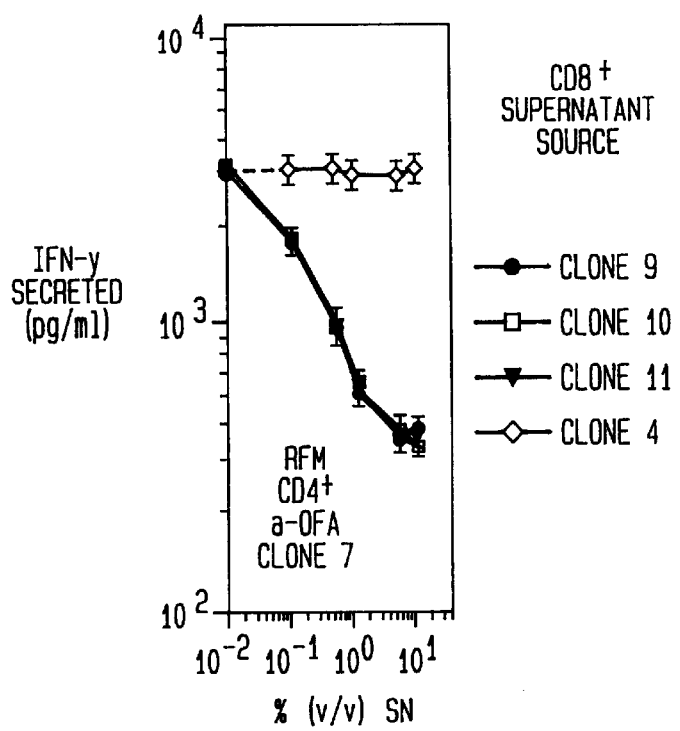
FIG. 2A shows the effect on IFN-γ secretion by OFA-specific CD4 RFM T cell clone 7 after preincubation with various amounts of culture supernatant from non-cytotoxic OFA-specific CD8 T cell clones 9, 10, and 11 or from $T_c$ clone 4 collected 1 week after restimulation of those clones with irradiated RFM 5T lymphoma cells+irradiated RFM T cell-depleted spleen cells+ IL-2.
Figure 2B:
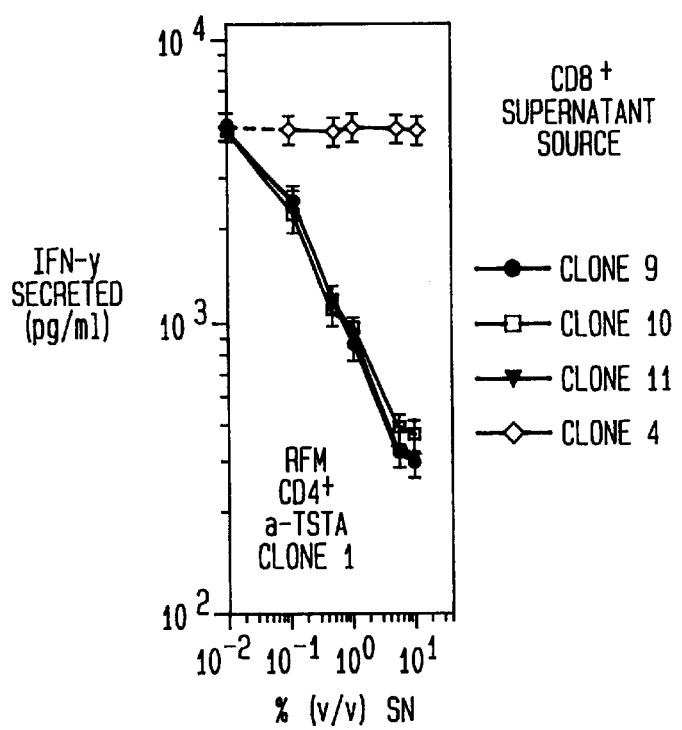
FIG. 2B shows the effect on IFN-γ secretion by 5T TSTA-specific CD4 RFM T cell clone 1 after preincubation with various amounts of culture supernatant collected from RFM non-cytotoxic T cell clones 9, 10, and 11 or from RFM $T_c$ clone 4 one week after restimulation of the clones as described in FIG. 2A above.

EXAMPLE 16
Inhibitor of interferon-γ secretion in the supernatants of anti-OFA, non-cytotoxic, CD8 T cell clones is an antigen-non-specific inhibitor To determine if the inhibitor of interferon-γ secretion was an antigen-specific suppressor factor or not, the experiment described above was repeated except that two RFM tumor-reactive CD4 T cell clones as target cells were used. Clone 7 is oncofetal antigen-specific (14) and clone 1 is specific for a 5T lymphoma TSTA (17). As before, the cytotoxic clone supernatant had no inhibitory activity at any concentration, but all three supernatants from the oncofetal antigen-specific, non-cytotoxic CD8 T cell clones inhibited both oncofetal antigen- and TSTA-specific T cell clone secretion of gamma interferon in a dose-dependent manner (FIGS. 2A and 2B). Once again 50% inhibition was found at 0.35 to 0.40% (v/v) supernatant concentration. That both clones are inhibited suggests that the active factor is not oncofetal antigen-spefic.

EXAMPLE 17
Inhibitor of interferon-γ secretion in the supernatants of anti-OFA, non-cytotoxic, CD8 RFM T cell clones is not MHC-restricted To demonstrate that the inhibitor is not MHC-restricted, a RFM CD4 T cell clone 7 that recognizes an oncofetal antigen peptide:H-$2^f$ class II protein complex (14) and the BALB/c CD4 T cell clone 5 that recognizes an oncofetal antigen peptide:H-$2^d$ class II protein complex (18) as the target cells for inhibition of gamma interferon secretion were utilized. If the inhibitor was MHC-restricted, it should only be able to inhibit the RFM clone.

Figure 3A:
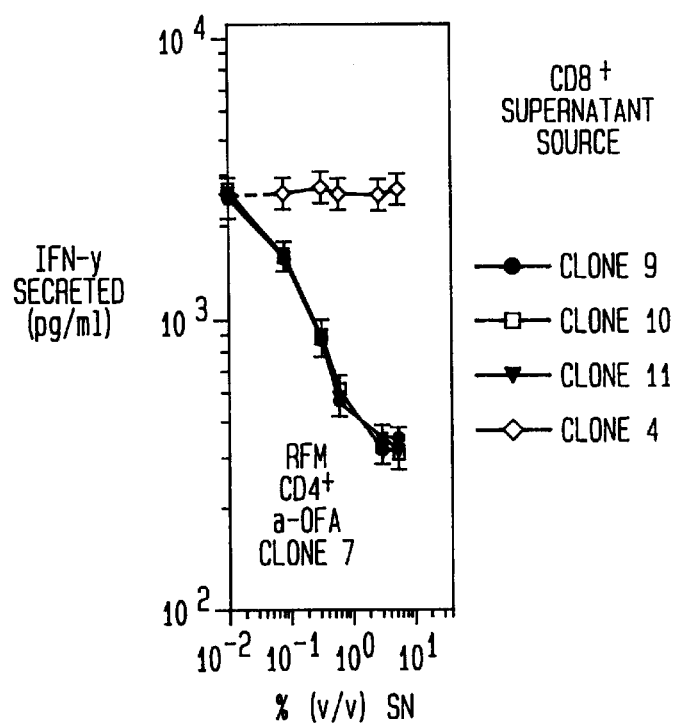
FIG. 3 shows that the inhibitory activity of culture supernatants from non-cytotoxic CD8, anti-OFA T cell clones for IFN-γ secretion is not MHC-restricted. The data are presented as mean IFN-γ concentration (pg/ml)±SEM. Experiments were repeated 3 times.
FIG. 3B shows the effect on IFN-γ secretion by RFM OFA-specific CD4 T cell clone 7 after preincubation with various amounts of culture supernatant collected from RFM non-cytotoxic CD8 T cell clones 9, 10, and 11 or from $T_c$ clone 4 one week after restimulation of those clones with irradiated RFM 5T lymphoma cells+ irradiated RFM T cell-depleted spleen cells+IL-2.
Figure 3B:
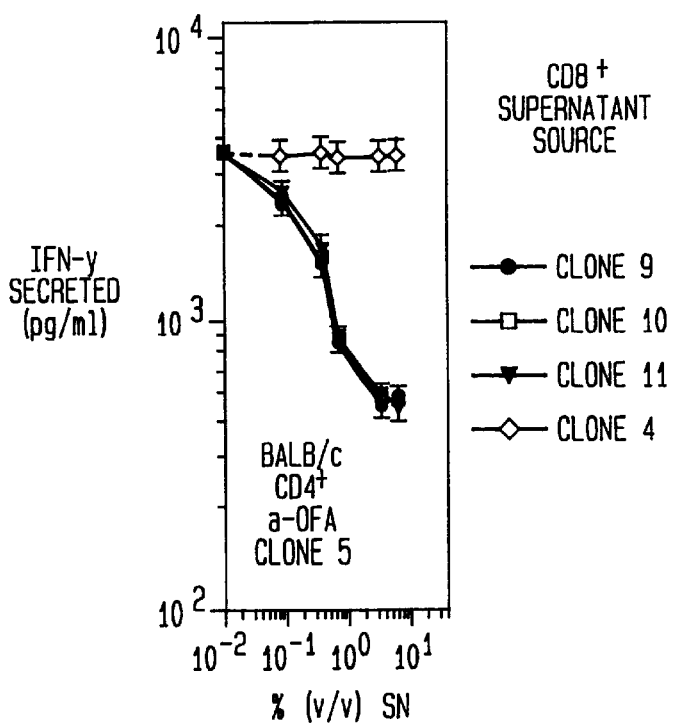

FIGS. 3A and 3B show that both RFM and BALB/c anti-oncofetal antigen clone interferon-γ secretion was inhibited in a dose-dependent manner by the culture supernatants of RFM non-cytototoxic T cell clones 9, 10, and 11. The inhibition was not the result of the presence of spent medium since no significant inhibiton was seen if as much as 10% supernatant from RFM anti-oncofetal antigen, cytotoxic CD8 T cell clone 4 was used (p>0.95). However, 50% inhibition of both BALB/c and RFM target cell secretion of interferon-γ was obtained at 0.35 to 0.40% (v/v) supernatant concentration from the RFM anti-oncofetal antigen, non-cytotoxic CD8 T cell clones tested. None of the inhibitory supernatants were significantly different from any of the others (p>0.94), but each was significantly more inhibitory than that of cytotoxic clone 4 (p<0.01). Also, the dose response of the inhibitory supernatants was not significantly different on the RFM target clone than on the BALB/c target clone (p<0.02). Therefore, the inhibitory factor was neither antigen-specific nor MHC-restricted and so may be a cytokine.

EXAMPLE 18
Supernatants from 5T lymphoma cell-stimulated non-cytotoxic T cell clones contain IL-10

Figure 4:
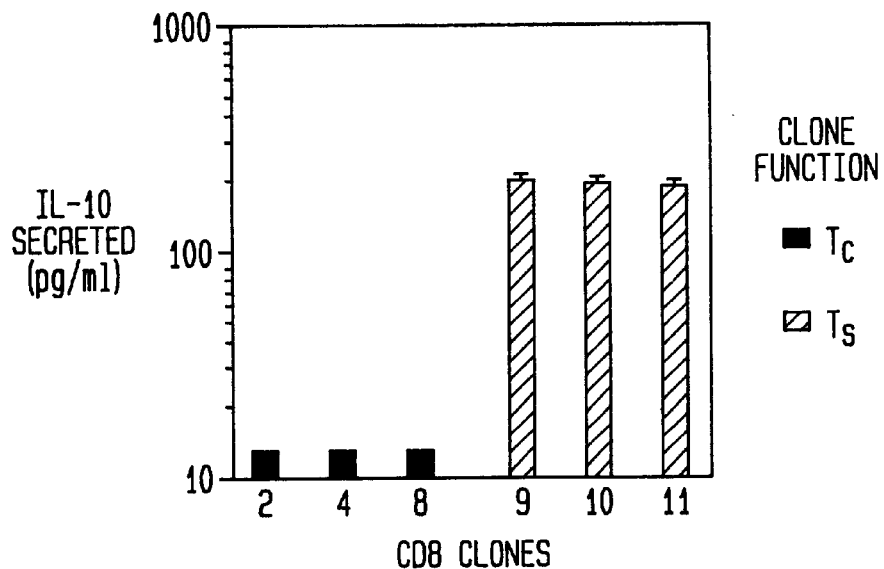
FIG. 4 shows the culture supernatants from RFM non-cytotoxic CD8, anti-OFA T cell clones, but not from RFM anti-OFA $T_c$ clones contain IL-10. Culture supernatants collected 1 week after restimulation of anti-OFA non-cytotoxic CD8+ clones and anti-OFA CD8+ $T_c$ clones with irradiated 5T lymphoma cells+irradiated, T cell-depleted, RFM spleen cells+IL-2 were assayed for IL-10 by a quantitative ELISA assay. Supernatants were collected three different times and the data are presented as mean IL-10 concentration (pg/ml)±SEM. The lowest amount of IL-10 detectable with this assay is 13 pg/ml.

Since IL-10 has been shown to be able to inhibit interferon-γ secretion by $CD4^+T_H1$ cells in mice (20) and since the inhibitor did not target cells by recognition of antigen:MHC expression, the supernatants of three different non-cytotoxic, anti-oncofetal antigen CD8 T cell clones and of three anti-oncofetal antigen $T_c$ cell clones for IL-10 secretion were assayed. FIG. 4 shows that while there was no IL-10 above the level of detection in the culture supernatants of 5T tumor cell-stimulated oncofetal antigen-specific, RFM $T_c$ clones 2, 4, and 8 (14), the supernatants from non-cytotoxic CD8 T cells had from 12.7–14.2 times more IL-10 than the $T_c$ clone supernatants after stimulation with irradiated 5T lymphoma cells. This difference was significant at the p<0.0001 level. The inhibitory supernatants were used in 100 μl volumes in inhibition assays and had a 50% inhibition concentration of 0.35 to 0.40% (FIGS. 1–3). Since those supernatants had from 177 to 209 pg/ml, the 50% inhibition concentration for IL-10 in these assays is 6.2–8.4 pg/well, if IL-10 is the inhibitor.

EXAMPLE 19
RFM 5T lymphoma cells are not the source of IL-10 in 5T cell-restimulated non-cytotoxic CD8 T cell clone cultures After 24 hour restimulation with irradiated 5T cells, both unselected populations of cells and $CD4^-$, $CD8^+$ T cells produced from 208 to 255 pg/ml of IL-10 in a second culture in IMDM+IL-2. However, neither the selected $CD4^+$, $CD8^+$ T cells (tumor cells) nor phenotype selected or unselected cytototoxic T cell clones produced any detectable IL-10. Neither the selected nor unselected non-cytotoxic T cell clone cultures were significantly different from one another in the amount of IL-10 produce (p>0.9).

EXAMPLE 20
Macrophages in the restimulated, non-cytotoxic T cell clone cultures are not the source of IL-10

Unselected, non-cytotoxic CD8 T cell clone cultures or cultures of $CD4^-$, $CD8^+$ T cell clone cultures produced 202–230 pg/ml of IL-10 in 24 hours after selection. The cytotoxic T cell clone cultures after restimulation did not produce detectable IL-10 and elimination of macrophages by anti-CD11b antibody+anti-rat IgG+complement did not affect the amount of IL-10 detected in cultures of either cytotoxic (p=1) or non-cytotoxic T cell clones (p>0.96) subsequent to restimulation.

Figure 5:
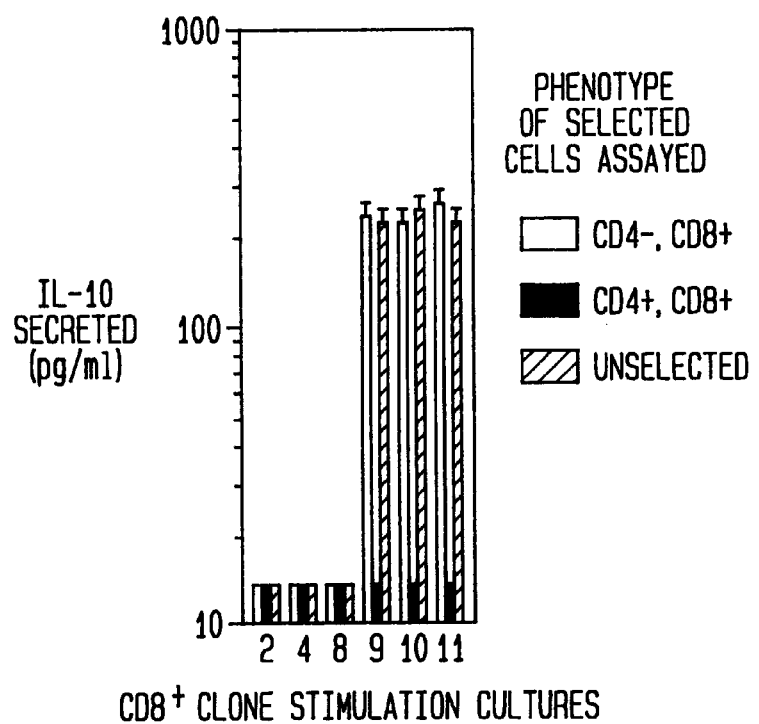
FIG. 5 shows the RFM 5T lymphoma cells are not the source of the IL-10. One week after restimulation, the CD8 cytotoxic and non-cytotoxic clone cells and the 5T lymphoma cells were separated by a combination of negative and positive selection with anti-CD4 and anti-CD8 monoclonal antibodies localized to Petri plates. After separation the unselected or selected populations were cultured for 48 hours and their supernatants collected and assayed for IL-10 by a quantitative ELISA assay. Supernatants were collected three different times and the data are presented as mean IL-10 concentration (pg/ml)±SEM. The lowest amount of IL-10 detectable with this assay is 13 pg/ml.

EXAMPLE 21
Anti-IL-10 neutralizes the non-cytotoxic CD8 T cell clone supernatant inhibition of interferon-γ secretion Monoclonal rat anti-mouse IL-10 IgM was titrated into the non-cytotoxic CD8 T cell clone supernatant:CD4 anti-oncofetal antigen T cell clone 4 incubation mixture to a final concentration varying from 1 to 25 μg/ml. As a control antibody, rat anti-mouse B220 IgM was titrated in to the same concentrations. FIG. 5A shows that even as little as 1 μg/ml of anti-IL-10 significantly increases the amount of interferon-γ secreted by clone 4 after stimulation with 5T lymphoma cells (p<0.03). As the amount of anti-IL-10 increases, the restoration of IFN-γ secretion increases until normal levels are reached by 25 μg/ml. Addition of this antibody had no effect on the $T_c$ clone 4 supernatant-treated CD4 clone secretion of IFN-γ (p>0.8). FIG. 5B shows that the presence of identical amounts of an irrelevant rat IgM monoclonal antibody does not block the non-cytotoxic CD8 T cell clone supernatant inhibition of anti-oncofetal antigen CD4 clone gamma interferon secretion (p>0.9).

Figure 6:
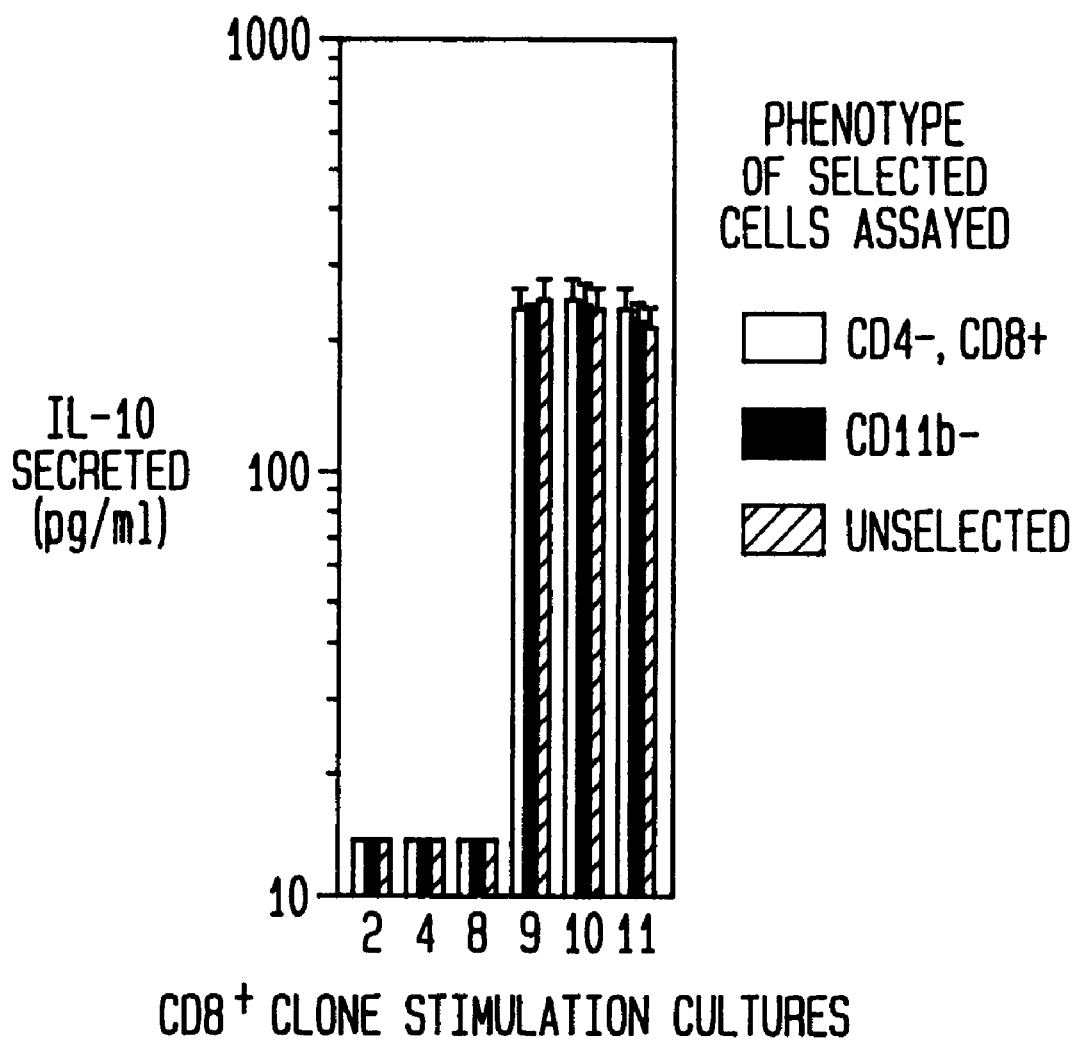
FIG. 6 shows the macrophages in the T cell clone stimulation cultures are not the source of IL-10. One week after restimulation of cytotoxic and non-cytotoxic CD8 T cell clones with irradiated 5T cells, the cultures are harvested and the T cell clones separated from the lymphoma cells by negative selection with CD4 antibody localized to Petri plates and positive selection with CD8 plates. Unselected cultures and cultures depleted of macrophages by anti-CD11b antibody+anti-rat IgG+complement cytotoxicity were cultured separately and 48 hours later supernatants were collected and assayed for IL-10 by ELISA assay. The data are presented as mean IL-10 concentration (pg/ml) ±SEM for 3 repeat experiments. The lowest amount of IL-10 detectable with this assay is 13 pg/ml.

EXAMPLE 22
Anti-IL-10 antibody neutralizes the non-cytotoxic CD8 T cell clone supernatant inhibition of OFA-specific CD8 cytotoxic T cell activity Since the supernatants from the non-cytotoxic CD8 T cell clones could inhibit tumor cell killing by oncofetal antigen-specific $T_c$ clone cells (14), the ability of anti-IL-10 monoclonal antibody to block inhibition by those supernatants of $T_c$ clone 1 killing of RFM 5T lymphoma cells was determined. As in the experiment above, the anti-IL-10 or anti-B220 antibodies were titrated into the 24 hour incubation of the target clone with 5% supernatant from non-cytotoxic CD8 clones 9, 10, or 11 or the same amount of supernatant from $T_c$ clone 4. FIG. 6A shows that as little as 5 μg/ml of anti-IL-10 antibody can significantly restore the cytotoxic activity of the anti-oncofetal antigen $T_c$ clone (p<0.02). As the dose of anti-IL-10 antibody increases, so does the amount of specific cytotoxicity obtained with maximal activity restored at 25 μg/ml anti-IL-10 (p=0.001). FIG. 6B shows that the isotype control anti-B220 antibody does not significantly restore the cytotoxic activity of the $T_c$ clone at any concentration used (p>0.9). Neither antibody affected the anti-5T cytotoxicity of $T_c$ clone clone 1 cells which had been pre-treated with $T_c$ clone 4 supernatant (which lacks IL-10 and is non-inhibitory) (p>0.8).

EXAMPLE 23
Anti-IL-10 antibody restores anti-5T cytotoxic activity to oncofetal antigen-specific, non-cytotoxic CD8 T cell clones Because IL-10 is in the culture supernatants of 5T lymphoma cell-stimulated non-cytotoxic CD8 T cell clones and anti-IL-10 blocks the inhibitory activity of those culture supernatants, that the oncofetal antigen-specific, non-cytotoxic CD8 T cell clones might themselves be inhibited from killing 5T cells by the presence of their own IL-10 during activation was examined. Therefore, 10 µg/ml anti-IL-10 or anti-B220 were added to the cytotoxicity assay containing non-cytotoxic T cell clones 9, 10, and 11 plus irradiated, T cell-depleted RFM spleen cells±irradiated 5T lymphoma cells plus IL-2. For a positive control, the anti-oncofetal antigen $T_c$ clone 1 was used.

FIG. 7 shows that in the presence of an anti-IL-10 antibody, all of the "non-cytotoxic" CD8 clones had significant cytotoxic activity against 5T cells (p<0.002). These clones, however, did not kill normal RFM spleen cells (data not shown). The amount of cytotoxicity is similar to that exhibited by clone 1 cells that had been pre-treated with the inhibitory supernatant in the presence of 10 µg/ml of anti-IL-10 (FIG. 5A). No cytotoxic activity was restored by addition of anti-B220, i.e., the effect is specific. Thus, the inhibitory clones can function as effectors if the suppression induced by the IL-10 secreted by the clones is neutralized.

EXAMPLE 24

Harvest of Human Mononuclear Cells (lymphocytes and monocytes)

Purification of human peripheral blood mononuclear leucocytes (lymphocytes and monocytes) is performed using a modification of the method of Boyum (68). The modification involves the use of sterile Ficoll sodium diatrizoate solution of the proper density, viscosity, and which is isotonic with human leucocytes (Ficoll-Paque Plus) instead of just Ficoll. This modification has been shown to be an easy one-step, rapid, reproducible method for the preparation of viable lymphocytes in high yield from peripheral blood (69–74).

a. Heparinized human blood is diluted 1:2 with RPMI-1640 tissue culture medium supplemented with 2 mM L-glutamine, 100 units/ml of Penicillin G and 100 µg/ml of Streptomycin.

b. The diluted blood is layered in 4 ml aliquots onto a 3 ml layer of Ficoll-Paque Plus in sterile 15 ml conical centrifuge tubes with an internal diameter of 1.3 cm. This layering is done so that minimal mixing of the blood and the Ficoll-Paque Plus occurs.

c. The tubes containing the Ficoll-Paque Plus and the blood are centrifuged at 400×g for 30 minutes at 18–20° C.

d. At the end of this centrifugation, the mononuclear leucocytes are located in a band between the plasma and the Ficoll-Paque Plus and the erythrocytes and granulocytes are in a pellet at the bottom of the tube.

e. The plasma is pipetted off and the mononuclear cell layer from each tube is pipetted into a 50 ml centrifuge tube (all tubes' mononuclear cell layers combined into one tube) and 3 cell volumes of RPMI-1640 (as prepared in 1a, above) is added to the 50 ml tube.

f. The mononuclear cell fraction tube is centrifuged at 60–100×g for 10 minutes at 18–20° C.

g. The supernatant is removed and the mononuclear cell pellet is resuspended in 10 ml of RPMI-1640 tissue culture medium supplemented as described in step 1a, above, and the cells transferred to a sterile 15 ml centrifuge tube and centrifuged at 60 100×g for 10 minutes at 18–20° C.

h. The supernatant is removed and discarded and cells resuspended in 1 ml of RPMI-1640 medium supplemented as in 1 a additionally containing 100 U/ml of recombinant human Interleukin-2, 10 U/ml of recombinant human Interferon-γ, and 10 units/ml of recombinant human Interleukin-6 and 10% (v/v) fetal calf serum (termed from here on complete RPMI-1640). IL-2 is utilized as a growth factor for T lymphocytes; -interferon is used to inhibit the outgrowth of Th2 helper T cells for antibody production (75); IL-6 is used to promote the outgrowth and function of T cytotoxic (TC) lymphocytes (76). The cells are counted for viability using Trypan blue dye exclusion on a hemacytometer with a light microscope (77).

EXAMPLE 25

Culture of Harvested Human Peripheral Blood Mononuclear Cells a. The harvested, counted human blood mononuclear leucocytes (lymphocytes and monocytes) were cultured in complete RPMI-1640 (as defined in 1 h above) after addition of 3000 rad-irradiated autologous tumor cells. The cultures were set up in appropriate volumes such that there were $5 \times 10^5$ viable blood mononuclear leucocytes/ml of culture and $5 \times 10^5$ viable irradiated autologous tumor cells/ml of culture.

b. During this culture all T lymphocytes capable of responding to antigens expressed by the tumor cells become activated and begin to proliferate while non-responding lymphocytes and all monocytes begin to die. Thus, every 2–3 days, cell viability counts were done and culture volume adjusted to allow a viable cell density permitting continued growth and viability of the responding cells. After about 1 week, the responding cells constitute the majority of remaining cells and culture volumes were expanded to keep the cell density from outgrowing the nutrients and growth factors present.

c. Every two weeks the tumor-reactive lymphocytes must be restimulated with irradiated autologous tumor cells in the presence of autologous irradiated peripheral blood mononuclear leucocytes to keep IL-2 growth factor receptors expressed so they can continue to proliferate.

d. After the initial two weeks of culture subsequent to purification of the mononuclear cells from human blood, the residual living cells were counted and cloned by limiting dilution at 0.2 cell/well in 96 well plates (78). Each well contained $10^5$ viable-irradiated autologous tumor cells (as the source of antigen) and $10^5$ viable-irradiated autologous peripheral blood mononuclear leucocytes to serve as antigen-presenting cells. After two weeks, those wells with one colony per well were harvested and expanded in the presence of irradiated autologous tumor cells and irradiated autologous peripheral blood mononuclear cells in complete RPMI-1640 medium.

e. After the clones were expanded and stabilized in their growth, they were cultured in RPMI-1640 which has all the supplements of complete RPMI-1640 except for -interferon and IL-6.

f. All cultures were done at 37° C. in a 95% air/5% $CO_2$ humidified atmosphere.

EXAMPLE 26

Determination of T Cell Clone Specificity by Proliferation in Response to Oncofetal Antigen Protein (OFA)

a. Two days before clones were to be restimulated with autologous tumor cells, some of the culture was harvested, washed, and a viability count done. 2–10,000 viable tumor-reactive clone cells were then seeded into each well of 96 well culture plates along with $5 \times 10^5$ viable 3000 rad-irradiated autologous peripheral blood mononuclear leucocytes plus various doses (15–300 ng/well) of purified OFA or non-tumor cell membrane proteins on nitrocellulose particles prepared using the method of Strandring and Williams (79) and Abou-Zeid et al. (80) as described previously (78). The cells are cultured in complete RPMI-1640 medium.

b. The cultures are incubated for 48 hours at 37° C. in a humidified 95% air/5% CO2 atmosphere.

c. The cultures are then pulsed with 10 µM 5-bromodeoxyuridine (100 µl/well) and cultured for another 24 hours under the conditions described in 3b.

d. At the end of that incubation, the plates are centrifuged at 300×g for 10 minutes at 4° C. to pellet the cells. The supernatant is then removed by tapping onto absorbent paper and the plates dried for 60 minutes at 60° C. After the hour of drying, the cells are fixed in 70% ethanol (200 μl/well) for 30 minutes at room temperature.

e. At the end of that incubation, the supernatant is removed by tapping onto absorbent paper and the protein-hinding areas of the plate blocked by a 30 minute room temperature incubation with 200 μl of 1% (w/v) nonfat dry milk protein in 50 mM Tris-HCl; 150 mM NaCl, pH 7.4.

f. After that incubation, the blocking buffer is removed by tapping the plates onto absorbent paper. Each well then receives 100 μl of 1:100 diluted anti-bromodeoxyuridine antibody which is conjugated with horseradish peroxidase and will bind to the DNA into which bromodeoxyuridine was incorporated during the S phase of the cell cycle of proliferating cells. This is incubated 90 minutes at room temperature.

g. After this incubation, the antibody solution is removed by tapping on absorbent paper and then the wells are rinsed 3 times with 200 μl of 0.1 M phosphate-buffered saline, pH 7.4, being careful not to disturb the cells on the bottom of the wells. Excess fluid is removed by tapping on absorbent paper.

h. 100 μl of room temperature-equilibrated substrate solution 3,3'5,5'-tetramethylbenzidine (TMB) in 15% (v/v) DMSO is added to each well. The plate is covered and mixed at room temperature until color development is sufficient for optical density measurement (5–30 minutes). When the required color intensity is achieved, the reaction is stopped by adding 25 μl of 1 M sulphuric acid to each well.

i. The optical density is read in a microELISA plate reader at 450 nm within 5 minutes. This assay is as sensitive as using [3H]-thymidine incorporation to measure proliferation (81), but has the advantage of not dealing with radioactive material.

EXAMPLE 26
Determination of T cell Subclass and Cytokine Produced by Cloned or Peripheral Blood T Lymphocytes To determine the subclass of OFA-specific T lymphocyte clones, whole peripheral blood T lymphocytes, or tumor reactive peripheral blood lymphocytes, flow cytometry is used while measuring CD4, CD8, and αβ or δγ T cell receptor expression.

a. First, the cells being observed are divided into two sets and stained for three color analysis. Both sets are stained with FITC-conjugated monoclonal anti-human CD4 and R-PE-conjugated monoclonal anti-CD8 and one is also stained with Cy-chrome conjugated monoclonal anti-human αβ TCR antibody while the other set is stained with Cy-chrome anti-human δγ TCR antibody. All three fluorochromes are excited by the 488 nm laser line, but will emit at 520 nm (FITC), 576 nm (R-PE), and 670 nm (Cy-Chrome).

b. To inhibit non-specific staining, a 10-fold excess of irrelevant monoclonal mouse antibodies of the same isotype is included in the buffer along with the three fluorochrome-conjugated antibodies. Also the buffer (Dulbecco's PBS, pH 7.2) contains 0.1% (v/v) sodium azide to block shedding of antigen.

c. The concentration of the antibodies needed to give optimal specific staining is determined experimentally whenever a new lot of antibody is obtained. All of these antibodies are obtained from Pharmingen, Inc.

d. These data indicate which clones are CD4+, which clones are CD8+, and which type of TCR each clone uses.

e. The same experimental methods are used with uncloned peripheral blood T lymphocytes freshly purified from cancer patients or normal controls or after being stimulated once with autologous tumor and then waiting for the tumor-reactive T lymphocytes to expand in culture.

f. These studies on freshly isolated mononuclear leucocytes determine if the cancer causes an overall change in CD4+ or CD8+ T cell frequencies or in the frequency of each, which uses a given type of T cell antigen receptor.

g. The experiments with expanded, but not cloned tumor-reactive T lymphocytes determine if any change is induced by the cancer in the frequency of these T cell subsets which can recognize tumor-expressed antigens.

To determine more clearly what functional activity these T cells have, three color analysis is utilized, but intracellular interferon-γ, intracellular IL-10, and surface CD4 or CD8 is observed. Interferon-gamma is made and secreted by Th1 helper cells for cell-mediated immunity and by CD8 cytotoxic T lymphocytes. IL-10 is a cytokine which inhibits cell-mediated immunity and gamma interferon secretion especially and it has been found to be made by OFA-specific CD8 T cell clones which are not cytotoxic, but through IL-10 can inhibit anti-tumor cytotoxic T cell function (82, 83).

h. The clones and tumor-reactive, uncloned peripheral blood mononuclear cell cultures from cancer patients is cultured with 3 μM monensin for 4–6 hours before cell harvest to block intracellular transport of proteins and thus have an accumulation of cytokines in the Golgi apparatus of the cells.

i. Freshly harvested and purified peripheral blood mononuclear leucocytes is placed in culture for 2 hours in complete RPMI-1640 supplemented as complete RPMI-1640 (as described in section 1h) except that no gamma interferon or IL-6 is present. After the 2 hours at 37° C. in a humidified 95% air/5% $CO_2$ atmosphere, monensin is added to 3 μM final concentration and the cells continued in culture for 4–6 hours.

j. In order to block nonspecific staining via Fc receptor binding, all cells are incubated with a 10-fold excess of irrelevant mouse monoclonal antibody of the same isotype as the fluorochrome-conjugated antibodies for 5 minutes before and continually during staining of the cells.

k. The cells are divided into two groups and stained with the experimentally determined optimal amount of FITC-conjugated monoclonal anti-human CD4 CD8 to determine which clones are making IL-10 (and are, thus, probably inhibitory, non-cytotoxic T cells) as well as determining which and how many CD4 clones are making either or both of these cytokines.

s. Using this technique with freshly harvested mononuclear leucocytes from cancer and normal patients, it is determined if there is an overall effect of the cancer on certain cytokine-producing T cell populations.

t. Using this technique with tumor-reactive, but uncloned peripheral blood T cells from cancer patients demonstrates whether the cancer has an effect on certain cytokine-producing tumor-reactive T cell populations.

u. While it has been shown that the amount of fluorescence detected for most intracellular cytokines is proportional to the amount found secreted by those same cells in culture supernatants (84, 85), that is not the case for interferon (84, 86). Thus, culture supernatants are taken 48 hours and 96 hours after restimulation of clones and of uncloned, tumor-reactive cancer patient peripheral blood T cells and assay by ELISA for interferon- as described previously (82).

The following references were cited herein:

1. Leffel, M. S., et al., *Cancer Res.* 37:4112, (1977).
2. North, R. J., et al., *J. Exp. Med.* 145:275, (1977).
3. Gershon, R. K., et al., *Nature* 213:674, (1967).
4. Vaage, J., *Cancer Res.* 31:1655, (1971).
5. Vose, B. M., et al., *Int. J. Cancer* 245:579, (1979).
6. Yu, A., et al., *N. Engl. J. Med.* 297:121, (1977).
7. Zarling, J. M., et al., *Cancer Immun Immunother.* 7:243, (1980).
8. Cone, L., et al., *J. Clin. Invest.* 43:2241, (1964).
9. Berg, D., et al., *J. Immunol.* 146:2865, (1991).
10. Bost, K. L., et al., *J. Immunol.* 154:718, (1995).
11. Smith, D. R., et al., *Am. J. Pathol.* 145:18, (1994).
12. Coggin, J. H., et al., *Am. J. Pathol.* 130:136, (1988).
13. Rohrer, S. D., et al., *J. Natl. Cancer Inst.* 84:602, (1992).
14. Rohrer, J. W., et al., *J. Immunol.* 154:2266, (1995).
15. Payne, W. J., Jr., et al., *J. Natl. Cancer Inst.* 75:527, (1985).
16. Rabin, H., et al., *J. Immunol.* 127:1852, (1981).
17. Rohrer, J. W., et al., *J. Immunol.* 152:754, (1994).
18. Decker, T., et al., *J. Immunol. Methods* 15:61, (1988).
19. Wysocki, L. J., et al., *Proc. Natl. Acad. Sci. USA* 75:2844, (1978).
20. Fiorentino, D. F., et al., *J. Exp. Med.* 170:2081, (1989).
21. Hellstrom, K. E., et al., *Int. J. Cancer* 21:317, (1978).
22. Wepsic, H. T., et al., *J. Natl. Cancer Inst.* 44:955, (1970).
23. Stephenson, K. R., et al., *Surgery* 105:523.
24. Lynch, D. H., et al., *Eur. J. Immunol.* 21:1403, (1991).
25. Barsoum, A. L., et al., *J. Biol. Resp. Modifiers* 8:579, (1989).
26. Restifo, N. P., et al., *J. Immunol.* 147:1453, (1991).
27. Chen, L., et al., *Cell* 71:1093, (1992).
28. Johnson, J. G., et al., *J. Immunol.* 152:429, (1994).
29. Harding, F. A., et al., *Nature* 356:607, (1992).
30. Damle, N. K., et al., *J. Immunol.* 148:1985, (1992).
31. Schwartz, R. H., *Science* 248:1349, (1990).
32. Lombardi, G. S., et al., *Science* 264:1587, (1994).
33. Moller, G., *Scand. J. Immunol.* 27:247, (1988).
34. DeSantis, R. G., et al., *Eur. J. Immunol.* 17:575, (1987).
35. Zheng, H., et al., *Proc. Natl Acad. Sci. USA* 86:3758, (1989).
36. Fairchild, R. L., et al., *J. Immunol.* 145:2001, (1990).
37. O'Garra, A., R., et al., *Eur. J. Immunol.* 22:711, (1992).
38. Rivas, J. M., et al., *J. Immunol.* 149:3865, (1992).
39. De Waal Malefyt, R., et al., *J. Exp. Med.* 174:1209, (1991).
40. Fiorentino, D. F., et al., *J. Immunol.* 146:3444, (1991).
41. Enk, A. H., et al., *J. Immunol.* 151:2390, (1993).
42. Ding, L., et al., *J. Immunol.* 148:3133, (1992).
43. De Waal Malefyt, R., et al., *J. Immunol.* 150:4754, (1993).
44. Schadene, L., et al., *J. Immunol.* 152:4368, (1994).
45. Powrie, F., et al., *Eur. J. Immunol.* 23:2223, (1993).
46. Li, L., et al., *J. Immunol.* 153:3967, (1994).
47. Ferguson, T. A., et al., *J. Exp. Med.* 179:1597, (1994).
48. Renie, J. and R. Rusting, *Sci. Amer.* Sept: 57–59 (1996).
49. Cox, R., *Intern. J. Rad. Biol.* 65: 57–64 (1994).
50. Levy, L. and K Bost, *Critical Reviews in Immunology* 16:31–57 (1996).
51. Chang, A. E. and S. Shu, *Critical Reviews in Oncology/Hematology* 22: 213–228 (1996).
52. Kavanaugh, D. Y. and D. P. Carbone, *Hematology/Oncology Clinics of North America:* 4:927–951 (1996).
53. Coggin, J. H., et al., *Internat. J. Rad. Biol.,* 1996 [in press].
54. Coggin, J. H., et al. *J. Natl. Cancer Inst.,* [in press] (1996).
55. Rohrer, S., et al., *J. Natl. Can. Inst.,* 84:602–609 (1992).
56. Rohrer, J. W., et al, *J. Immunol.* 152: 754–764 (1994).
57. Rohrer, J., et al., *J. Immunol.,* 154: 2266–2280 (1995).
58. Rohrer, J. and Coggin, J. H., *J. Immunol.,* 155: 5719–5727 (1995).
59. Henderson, R. A. and O. J. Finn., *Advances in Immunology* 62:217–256 (1996).
60. J. H. Coggin, Jr. Shared Cross-Protective OFAs on Chemically Induced Rodent Sarcomas. Immunology Today. 10(3):76–78 (1989).
61. J. H. Coggin, Jr., *Molecular Biotherapy* 1(4):223–228 (1989).
62. A. L. Barsoum and J. H. Coggin, Jr., *Journal of Biological Response Modifiers.* 8:579–592 (1989).
63. Barsoum, A. and Coggin, J., Jr., *Inter. J. Cancer* 48:248–252 (1991).
64. Barsoum, A. and Coggin, J., Jr., *Int. J. Biochem.* 24:483–489 (1993).
65. Coggin, J. et al., *Archives of Otolaryngology-Head and Neck Surgery* 119: 1257–1266 (1993).
66. Rashid, Haroon-Ur, et al, *J. Nat'l Cancer Inst* 86:515–526 (1994).
67. W. J. Payne, Jr. and J. H. Coggin, Jr., *J. Nat'l Cancer Inst.* 75(3):115–132 (1985).
68. Boyum, A., *Nature* 204:793 (1964)
69. Harris, R and E. O. Ukaejiofo, *Brit. J. Haematol.* 18:229 (1970).
70. Ting, A. and P. J. Morris, *Vox Sang.* 20:561 (1971).
71. Fotino, M., E. et al., *Ann. Clin. Lab. Sci.* 1:131 (1971).
72. Bain, B. and K. Pshyk, *Transplantation Proc.* 4:163 (1972).
73. Wybran, J., et al., *J. Immunol.* 110:1157 (1973).
74. Fotino, M., et al., *Vox Sang* 21:469 (1971).
75. Gajewski, T. F. and F. W. Fitch, *J. Immunol.* 140:4245 (1988).
76. Rogers, L. A., et al., *J. Immunol. Methods* 15:61 (1991).
77. Phillips, H. J. In: Tissue Culture:Methods and Applications. P. F. Kruse, Jr., ed. Academic Press, New York, pp. 406–408 (1973).
78. Rohrer, J. W., et al., *J. Immunol.* 152:754 (1994).
79. Standring, R. and A. F. Williams, *Biochem. Biophys. Acta* 508:85 (1978).
80. Abou-Zeid, C., et al., *J. Immunol. Methods* 98:5 (1987).
81. Porstmann, T., et al., *J. Immunol. Methods* 82:169 (1985).

82. Rohrer, J. W.,et al., *J. Immunol.* 154:2266 (1995).

83. Rohrer, J. W. and J. H. Coggin, Jr., *J. Immunol.* 155:5719 (1995).

84. Elson, L. H., et al., *J. Immunol.* 154:4294 (1995).

85. Jung, T., et al., *J. Immunol. Methods* 159:197 (1993).

86. Vikingson, A., et al., *J. Immunol. Methods* 173:219 (1994).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. A method of determining whether cancer treatment is successful, comprising:

obtaining a sample of T-lymphocytes from a cancer patient undergoing cancer therapy; wherein said cancer is characterized by expression of 44 kD oncofetal antigen (OFA);

cloning said T-lymphocytes including CD8 cytotoxic T-lymphocytes and T-cells making IL-10, wherein cloned T-lymphocytes comprise OFA-specific T-cells;

contacting said T-lymphocytes with a composition comprising the 44 kD OFA, thereby stimulating said OFA-specific T-cells; and determining the relative frequency of said OFA-specific T-cells making IL-10 to said OFA-specific CD8 cytotoxic T-cells, wherein when said frequency of said OFA-specific CD8 cytotoxic T-cells is high and said frequency of said OFA-specific T-cells making IL-10 is low, said cancer therapy is successful.

2. A kit for practicing the method of claim 1, comprising:

interleukin-2 and interleukin-6;

a T-lymphocyte growth medium;

autologous antigen processing cells;

44 kD OFA;

at least one reagent for measuring T-cell DNA stimulation; and

CD4, CD8 and IL-10 phenotyping reagents.

* * * * *

UNITED STATES PATENT AND TRADEMARK OFFICE
CERTIFICATE OF CORRECTION

PATENT NO. : 6,335,174 B1
DATED : January 1, 2002
INVENTOR(S) : Joseph H. Coggin, Adel L. Barsoum and James W. Rohrer It is certified that error appears in the above-identified patent and that said Letters Patent is hereby corrected as shown below:

Title page,
Item [75], please change the order of inventors to -- Joseph H. Coggin, Jr., Adel L. Barsoum and James W. Rohrer --.
Item [57], ABSTRACT,
Line 3, delete the word "an".

Column 1,
Line 37, "b y" should read -- by --.

Column 2,
Line 42, "response" should read -- responses --.

Column 4,
Line 22, "succes" should read -- success --.

Column 5,
Line 31, "contain" should read -- containing --.

Column 7,
Line 35, "b y" should read -- by --.
Line 48, after "some" insert -- of --.
Line 49, after "responses" insert -- . --.

Column 8,
Line 21, "Fc" should read -- FC --.
Line 36, "Tc" should read -- TC --.

Column 9,
Line 28, "Tc" should read -- TC --.

Column 12,
Line 11, delete "the" second occurrence.

Column 14,
Line 4, "T492" should read -- 492 --.

Column 17,
Line 43, "were" should read -- was --.

UNITED STATES PATENT AND TRADEMARK OFFICE
CERTIFICATE OF CORRECTION

Figure 7A:
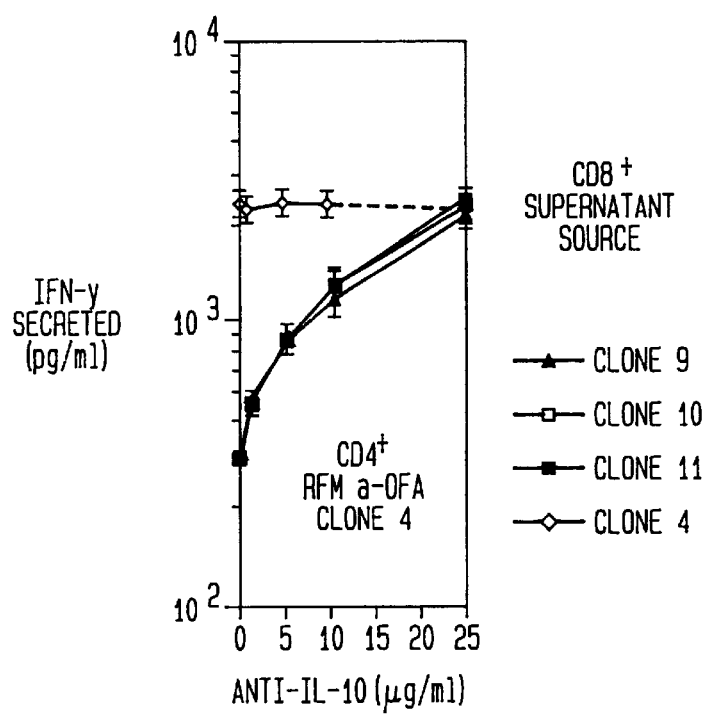
FIG. 7 shows the monoclonal rat anti-mouse IL-10 IgM antibody (A), but not monoclonal rat anti-mouse B220 IgM antibody (B), neutralizes the inhibition of IFN-γ secretion by non-cytotoxic, CD8, anti-OFA T cell clone culture supernatants. The data are presented as mean IFN-γ concentrations±SEM for 3 repeats of the experiment. The supernatants from RFM non-cytotoxic CD8 T cell clones 9, 10, and 11 and $T_c$ clone 4 were collected 1 week after restimulation of those clones with irradiated 5T lymphoma cells+irradiated, T cell-depleted, RFM spleen cells+IL-2 and added at 10% (v/v) final concentration to cultures of RFM OFA-specific CD4 T cell clone 4 during its restimulation with irradiated 5T lymphoma cells+irradiated, T cell-depleted RFM spleen cells+IL-2.
Figure 7B:
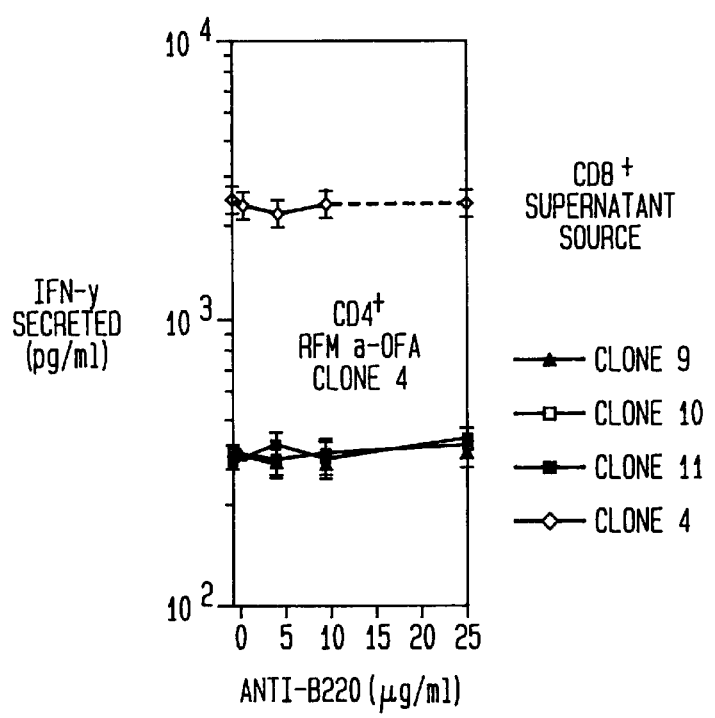
Figure 8A:
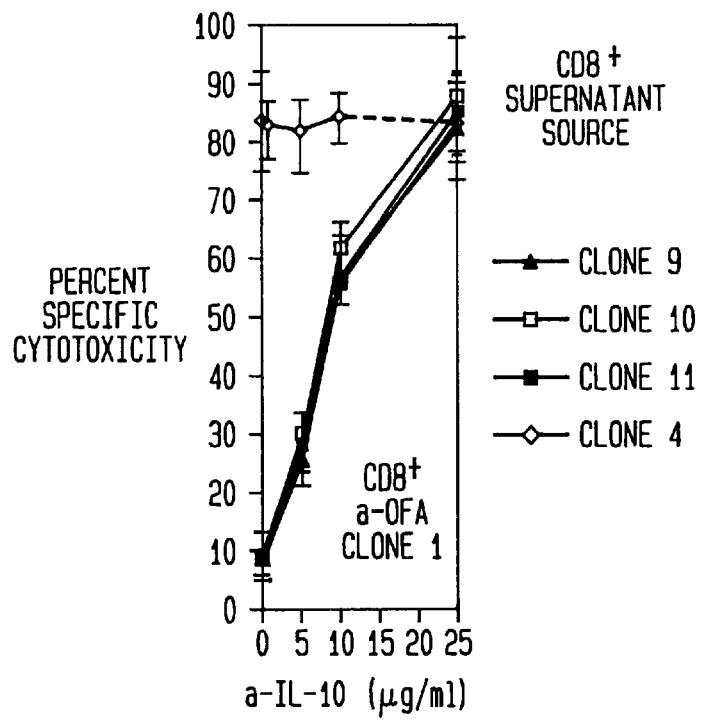
FIG. 8 shows the monoclonal rat anti-mouse IL-10 IgM antibody (FIG. 8A), but not monoclonal rat anti-mouse B220 IgM antibody (FIG. 8B), neutralizes the inhibition of anti-5T cytotoxicity of $T_c$ clone 1 by non-cytotoxic, CD8, anti-OFA T cell clone culture supernatants. The data are presented as mean % specific cytotoxicity±SEM for 3 repeats of the experiment. The supernatants from non-cytotoxic T cell clones 9, 10, and 11 and $T_c$ clone 4 were added at 10% (v/v) final concentration. The effector cell-:target cell ratio was 50:1 and the culture supernatants were added to 5% (v/v) final concentration.
Figure 8B:
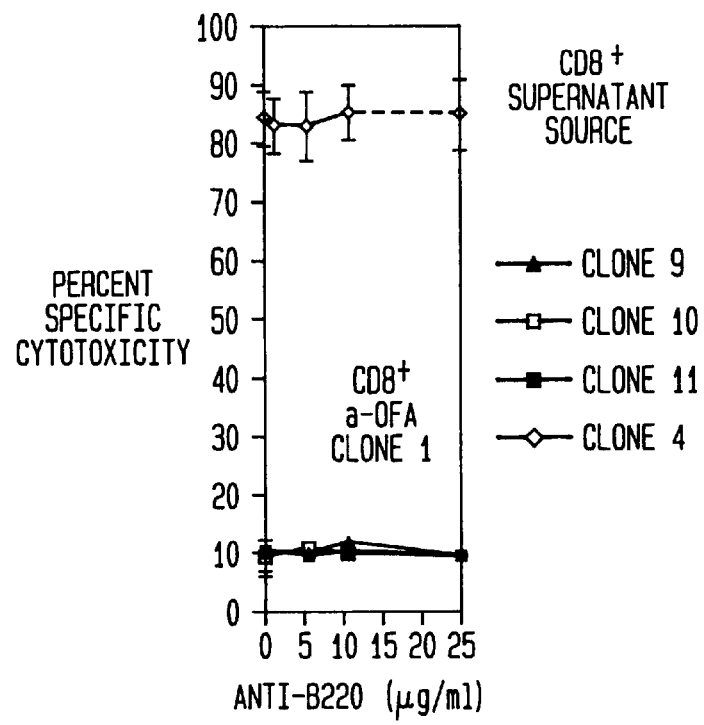

PATENT NO. : 6,335,174 B1
DATED : January 1, 2002
INVENTOR(S) : Joseph H. Coggin, Adel L. Barsoum and James W. Rohrer It is certified that error appears in the above-identified patent and that said Letters Patent is hereby corrected as shown below:

Column 20,
Line 22, "FIG. 5A" should read -- FIG. 7A --.
Line 29, "FIG. 5B" should read -- FIG. 7B --.
Line 47, "FIG. 6A" should read -- FIG. 8A --.
Line 52, "FIG. 6B" should read -- FIG. 8B --.

Figure 9:
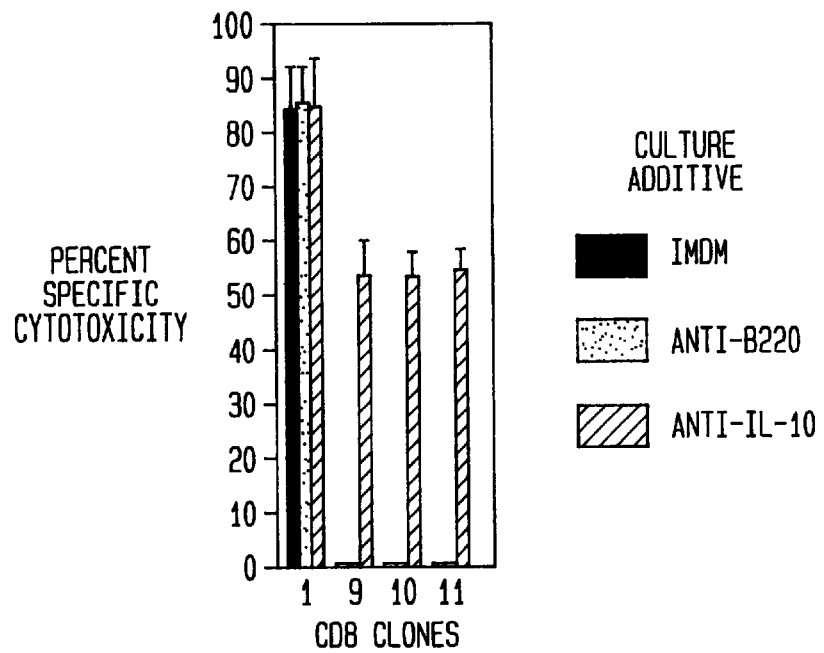
FIG. 9 shows the non-cytotoxic, CD8+, anti-OFA T cell clones become able to lyse RFM 5T lymphoma cells if monoclonal anti-IL-10, but not anti-B220, IgM is added for 24 hours before and during the cytotoxicity assay. The data are presented as mean % specific cytotoxicity±SEM for 3 repeat experiments. The effector cell:target cell ratio was 50:1 and the anti-IL-10 or anti-B220 IgM was added to a final concentration of 10 μg/ml.
Figure 10:
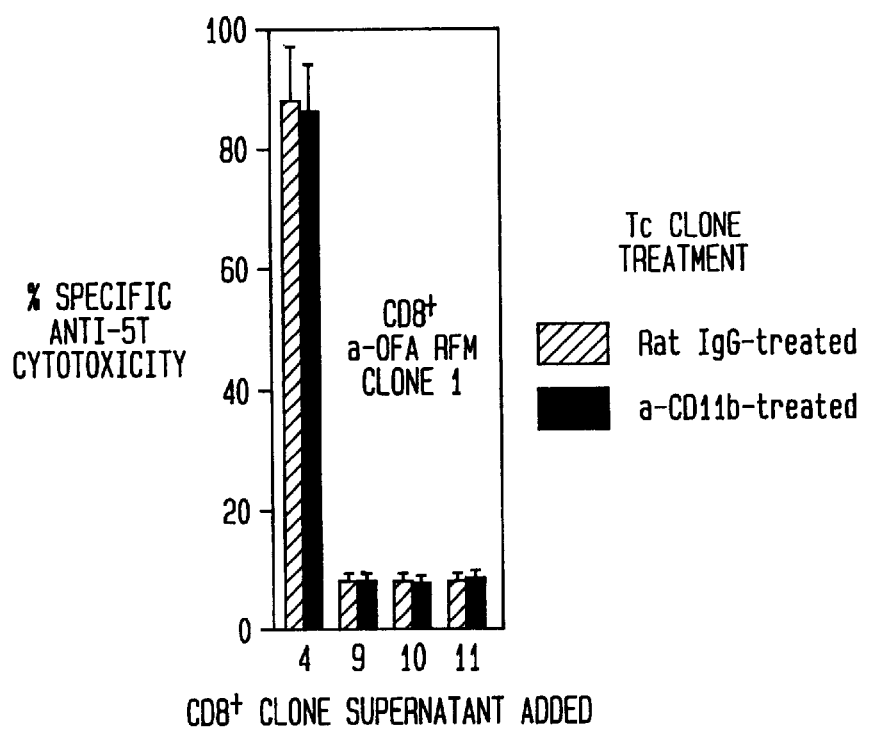
FIG. 10 shows the macrophages in the cytotoxic clone 1 culture are not the targets for the non-cytotoxic supernatant inhibition of $T_c$ clone activity. 24 hours before the regular 2 week restimulation of cytotoxic clone 1 by irradiated 5T lymphoma cells, the cells are harvested and treated with rat anti-mouse CD11b antibody+anti-rat IgG+complement to deplete any macrophages still present or with normal rat IgG+anti-rat IgG+complement as an isotype control antibody. The remaining cells are then cultured for 24 hours in IMDM containing 25% (v/v) final concentration of cytotoxic clone 4 supernatant or noncytotoxic clones 9, 10, or 11 supernatant. After the 24 hour incubation, the cells are washed in IMDM and assayed for anti-5T cytotoxic activity. This was repeated 3 times and the data represent the mean ±SEM of % specific cytotoxicity.

Column 21,
Line 8, "FIG. 7" should read -- FIG. 9 --.

Column 23,
Line 9, "hinding" should read -- binding --.

Column 24,
Line 26, "is" should read -- are --.
Line 32, "is" should read -- are --.

Signed and Sealed this

Twenty-eighth Day of January, 2003

JAMES E. ROGAN
*Director of the United States Patent and Trademark Office*